(12) United States Patent
Wilson et al.

(10) Patent No.: US 11,478,162 B2
(45) Date of Patent: Oct. 25, 2022

(54) FLOW MEASUREMENT USING IMAGE DATA

(71) Applicant: ACIST Medical Systems, Inc., Eden Prairie, MN (US)

(72) Inventors: Robert F. Wilson, Roseville, MN (US); Todd Suchecki, Robbinsdale, MN (US); Thomas M. Snyder, Saint Paul, MN (US); Alan Evans, Otsego, MN (US); Bryan Brutlag, Edina, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 754 days.

(21) Appl. No.: 16/420,353

(22) Filed: May 23, 2019

(65) Prior Publication Data
US 2019/0357778 A1    Nov. 28, 2019

Related U.S. Application Data

(60) Provisional application No. 62/675,348, filed on May 23, 2018.

(51) Int. Cl.
*A61B 5/0275* (2006.01)
*G06T 7/246* (2017.01)
(Continued)

(52) U.S. Cl.
CPC .......... *A61B 5/0275* (2013.01); *G06T 7/0016* (2013.01); *G06T 7/248* (2017.01); *G06V 10/751* (2022.01); *G06T 2207/30104* (2013.01)

(58) Field of Classification Search
None
See application file for complete search history.

(56) References Cited

U.S. PATENT DOCUMENTS

| | | | |
|---|---|---|---|
| 2,627,270 | A | 2/1953 | Glass |
| 4,044,757 | A | 8/1977 | McWhorter et al. |

(Continued)

FOREIGN PATENT DOCUMENTS

| | | |
|---|---|---|
| CN | 87202114 U | 4/1988 |
| CN | 1617686 A | 5/2005 |

(Continued)

OTHER PUBLICATIONS

Shaw et al. (Pulsed-injection method for blood flow velocity measurement in intra-arterial digital subtraction angiography, Radiological society of north America, vol. 160, No. 2, 1986] (Year: 1986).*

(Continued)

*Primary Examiner* — Amelie R Davis
*Assistant Examiner* — Marjan Saboktakin
(74) *Attorney, Agent, or Firm* — Fredrikson & Byron, P.A.

(57) ABSTRACT

Embodiments for assessing flow at an anatomical region of interest are disclosed. One embodiment uses pulsed contrast media injections at a known frequency along with corresponding image data to derive a measurement of blood flow velocity at the region of interest. Another embodiment uses incremental changes in known contrast media injection flow rates to match the blood flow rate relative to one of these known contrast media injection flow rates based on the presence of a particular indicia in image data. For example, this indicia can be the flow of contrast media out from a coronary artery back into the aorta or the onset of a steady state pixel density. A further embodiment uses contrast media injections that are synchronized with the cardiac cycle. For example, contrast media injections can be synchronized with the diastolic and/or systolic phases and used to measure blood flow accordingly.

17 Claims, 9 Drawing Sheets

(51) Int. Cl.
  *G06T 7/00* (2017.01)
  *G06V 10/75* (2022.01)

(56) References Cited

U.S. PATENT DOCUMENTS

| | | | |
|---|---|---|---|
| 4,084,606 A | 4/1978 | Mittleman | |
| 4,250,887 A | 2/1981 | Dardik | |
| 4,462,409 A | 7/1984 | Pace et al. | |
| 4,819,684 A | 4/1989 | Zaugg et al. | |
| 5,097,841 A | 3/1992 | Moriuchi et al. | |
| 5,098,405 A | 3/1992 | Peterson et al. | |
| 5,176,658 A | 1/1993 | Ranford | |
| 5,190,067 A | 3/1993 | Paradis et al. | |
| 5,267,964 A | 12/1993 | Karg | |
| 5,573,515 A | 11/1996 | Wilson et al. | |
| 5,800,397 A | 9/1998 | Wilson et al. | |
| 5,840,026 A | 11/1998 | Uber, III et al. | |
| 5,843,044 A | 12/1998 | Moorehead | |
| 5,882,343 A | 3/1999 | Wilson et al. | |
| 6,050,450 A | 4/2000 | Gardos | |
| 6,099,502 A | 8/2000 | Duchon et al. | |
| 6,182,698 B1 | 2/2001 | Barak | |
| 6,221,045 B1 | 4/2001 | Duchon et al. | |
| 6,254,835 B1 | 7/2001 | Feygin | |
| 6,344,030 B1 | 2/2002 | Duchon et al. | |
| 6,447,481 B1 | 9/2002 | Duchon et al. | |
| 6,569,117 B1 | 5/2003 | Ziv et al. | |
| 6,638,258 B2 | 10/2003 | Schwartz et al. | |
| 6,656,157 B1 | 12/2003 | Duchon et al. | |
| 6,708,714 B1 | 3/2004 | Mijers | |
| 6,733,477 B2 | 5/2004 | Cowan et al. | |
| 6,746,427 B2 | 6/2004 | Duchon et al. | |
| 6,752,789 B2 | 6/2004 | Duchon et al. | |
| 6,945,959 B2 | 9/2005 | Duchon et al. | |
| 7,094,216 B2 | 8/2006 | Trombley, III et al. | |
| 7,128,729 B2 | 10/2006 | Duchon et al. | |
| 7,153,288 B2 | 12/2006 | Duchon et al. | |
| 7,267,666 B1 | 9/2007 | Duchon et al. | |
| 7,326,186 B2 | 2/2008 | Trombley, III et al. | |
| 7,357,785 B2 | 4/2008 | Duchon et al. | |
| 7,389,788 B2 | 6/2008 | Wilson et al. | |
| 7,566,326 B2 | 7/2009 | Duchon et al. | |
| 7,581,559 B2 | 9/2009 | Bausmith, III | |
| 7,610,936 B2 | 11/2009 | Spohn et al. | |
| 7,617,837 B2 | 11/2009 | Wilson et al. | |
| 7,662,124 B2 | 2/2010 | Duchon et al. | |
| 7,703,483 B2 | 4/2010 | Hartman et al. | |
| 8,412,312 B2 | 4/2013 | Judell et al. | |
| 2002/0065467 A1 | 5/2002 | Schutt | |
| 2002/0103437 A1 | 8/2002 | Jibiki | |
| 2003/0018252 A1 | 1/2003 | Duchon et al. | |
| 2003/0122095 A1 | 7/2003 | Wilson et al. | |
| 2005/0230575 A1 | 10/2005 | Zelenski et al. | |
| 2005/0234407 A1 | 10/2005 | Spohn et al. | |
| 2005/0234428 A1 | 10/2005 | Spohn et al. | |
| 2006/0079768 A1 | 4/2006 | Small et al. | |
| 2006/0167415 A1 | 7/2006 | Nemoto | |
| 2006/0178632 A1 | 8/2006 | Trombley et al. | |
| 2006/0180202 A1 | 8/2006 | Wilson et al. | |
| 2006/0184122 A1 | 8/2006 | Nemoto | |
| 2007/0055202 A1 | 3/2007 | Duchon et al. | |
| 2007/0161970 A1 | 7/2007 | Spohn et al. | |
| 2007/0167919 A1 | 7/2007 | Nemoto et al. | |
| 2007/0179487 A1 | 8/2007 | Tearney et al. | |
| 2007/0244435 A1 | 10/2007 | Hicks | |
| 2007/0249936 A1 | 10/2007 | Deckman et al. | |
| 2008/0086087 A1 | 4/2008 | Spohn et al. | |
| 2008/0091142 A1 | 4/2008 | Trombley et al. | |
| 2008/0103437 A1 | 5/2008 | Duchon et al. | |
| 2008/0161634 A1 | 7/2008 | Nemoto et al. | |
| 2008/0183131 A1 | 7/2008 | Duchon et al. | |
| 2008/0300483 A1 | 12/2008 | Nemoto et al. | |
| 2009/0131765 A1 | 5/2009 | Roschak et al. | |
| 2009/0149743 A1 | 6/2009 | Barron et al. | |
| 2009/0221914 A1 | 9/2009 | Barrett et al. | |
| 2009/0234231 A1 | 9/2009 | Knight et al. | |
| 2009/0304593 A1 | 12/2009 | Frinking et al. | |
| 2009/0312740 A1 | 12/2009 | Kim et al. | |
| 2010/0019178 A1 | 1/2010 | Wilson et al. | |
| 2010/0094133 A1 | 4/2010 | Yoshiara et al. | |
| 2010/0113924 A1 | 5/2010 | Hajicek et al. | |
| 2010/0249588 A1 | 9/2010 | Knight | |
| 2011/0071404 A1 | 3/2011 | Schmitt et al. | |
| 2011/0071405 A1 | 3/2011 | Judell et al. | |
| 2011/0077528 A1 | 3/2011 | Kemp et al. | |
| 2011/0196255 A1 | 8/2011 | Kassab | |
| 2012/0022360 A1 | 1/2012 | Kemp | |
| 2013/0216114 A1 | 8/2013 | Courtney et al. | |
| 2014/0121513 A1 | 5/2014 | Tolkowsky et al. | |
| 2014/0180083 A1 | 6/2014 | Hoseit | |
| 2015/0324962 A1 | 11/2015 | Itu et al. | |
| 2017/0325769 A1* | 11/2017 | Venugopal | A61B 6/486 |
| 2021/0244371 A1* | 8/2021 | Zhang | A61B 6/12 |

FOREIGN PATENT DOCUMENTS

| | | |
|---|---|---|
| CN | 101039711 A | 9/2007 |
| CN | 101355975 A | 1/2009 |
| EP | 331526 A1 | 9/1989 |
| JP | 62221335 A | 9/1987 |
| JP | 2001178720 A | 7/2001 |
| JP | 2001245862 A | 9/2001 |
| JP | 2002210007 A | 7/2002 |
| WO | 02064195 A2 | 8/2002 |
| WO | 03050491 A2 | 6/2003 |
| WO | 2005070299 A1 | 8/2005 |
| WO | 2005110007 A2 | 11/2005 |
| WO | 2007062315 A2 | 5/2007 |

OTHER PUBLICATIONS

Olin et al. ("Spillover flowmeter; a preliminary report", 1964) hereinafter "Olin". (Year: 1964).*

Molloi et al. ("Estimation of coronary artery hyperemic blood flow based on arterial lumen volume using angiographic images", In. J. Cardio. Imag. 2012) (Year: 2012).*

Shaw, C.G. et al., "Pulsed-injection method for blood flow velocity measurement in intraarterial digital subtraction angiography," Radio Radiological Society of North America, Inc., US, vol. 160, No. 2, Aug. 1, 1986, Abstract.

PCT Invitation and Partial Search Report and Provisional Opinion dated Aug. 19, 2019 for related International Application No. PCT/US2019/033659, 11 pgs.

PCT International Search Report and Written Opinion dated Oct. 9, 2019 for related International Application No. PCT/US2019/033659, 19 pgs.

Holdsworth, D.W. et al., Quantitative antiographic blood-flow measurement using pulsed intra-arterial injection, The International Journal of Medical Physics Research and Practice, Oct. 1, 1999, retrieved on May 14, 2018 from https://aapm.onlinelibrary.wiley.com/doi/pdf/10.1118/1.598733, Abstract.

Bazilevs et al., "From Imaging to Prediction: Emerging Non-Invasive Methods in Pediatric Cardiology," Progress in Pediatric Cardiology, vol. 30, No. 1-2, 2010, pp. 81-89.

Chen et al., "Phase Insensitive Homomorphic Image Processing for Speckle Reduction," Ultrasonic Imaging, vol. 18, Article 0007, 1996, pp. 122-139.

Ledoux et al., "Angle-Independent Motion Measurement by Correlation of Ultrasound Signals Assessed with a Single Circular-Shaped Transducer," Ultrasonic Imaging, vol. 21, 1999, pp. 216-240.

Lupotti et al., "Quantitative IVUS Blood Flow Using an Array Catheter," Computers in Cardiology, vol. 28, 2001, pp. 5-8.

Revell et al., "Computer Vision Elastography: Speckle Adaptive Motion Estimation for Elastography Using Ultrasound Sequences," IEEE Transactions on Medical Imaging, vol. 24, No. 6, Jun. 1, 2005, pp. 755-766.

Wagner et al., "Statistics of Speckle in Ultrasound B-Scans," IEEE Transactions on Sonics and Ultrasonics, vol. 30, No. 3, May 1983, pp. 156-163.

(56) References Cited

OTHER PUBLICATIONS

Wang et al., "Contrast Medium Assisted Fluid Flow Measurements," IEEE Transactions on Ultrasonics, Ferroelectric, and Frequency Control, vol. 42, No. 2, Mar. 1995, pp. 309-315.

Webster et al., "Measurement of Flow and Volume of Blood," Medical Instrumentation Application and Design, Wiley, 4th Edition, 2009, pp. 341-342.

Wilson et al., "Measurement of Two-Dimensional Blood Velocity Vectors by the Ultrasonic Speckle Projection Technique," Ultrasonic Imaging, vol. 15, 1993, pp. 286-303.

Xu, "Two-Dimensional Blood Flow Velocity Estimation Using Ultrasound Speckle Pattern Dependence on Scan Direction and Velocity," Aug. 1, 2012, 169 pages.

* cited by examiner

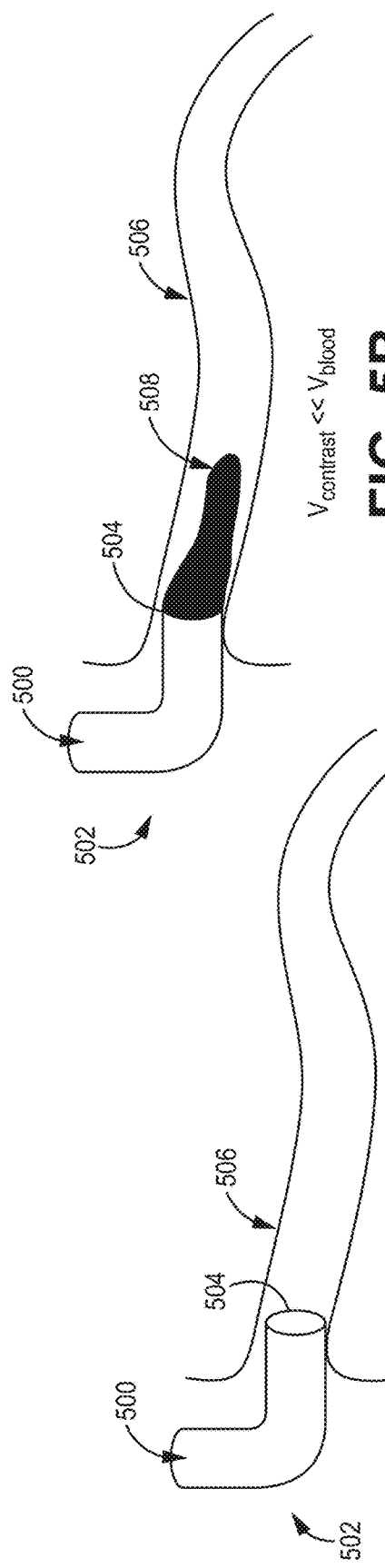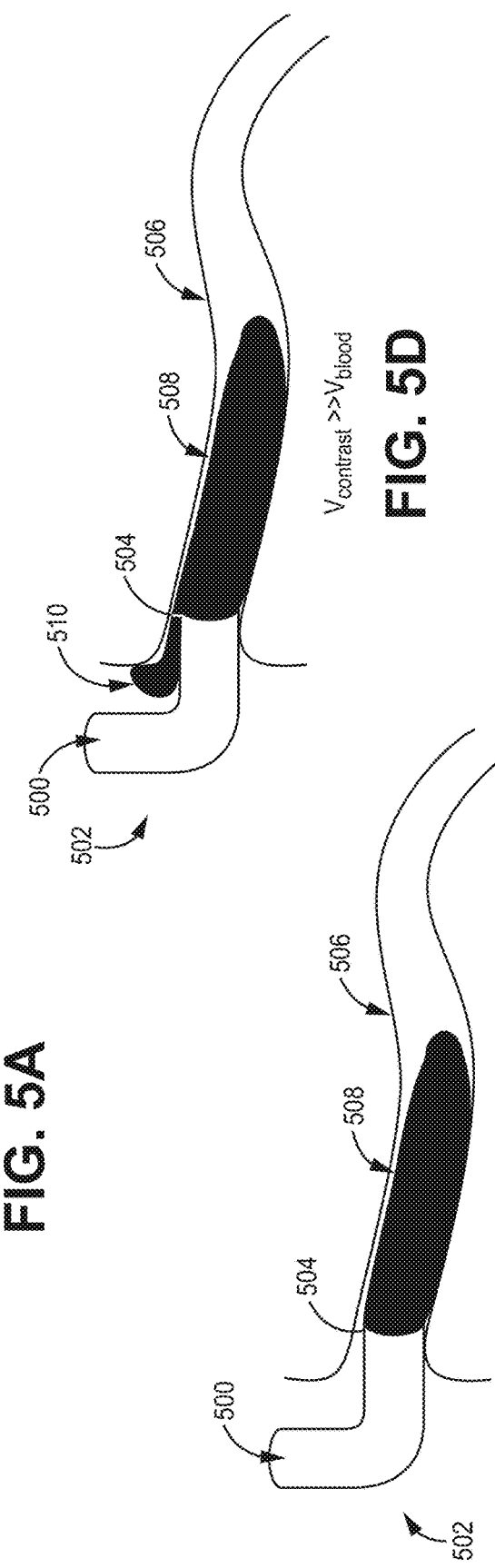

FLOW MEASUREMENT USING IMAGE DATA

RELATED APPLICATION

This application claims the benefit of U.S. Provisional Application No. 62/675,348 filed May 23, 2018, the contents of which are hereby incorporated by reference.

TECHNICAL FIELD

This disclosure relates generally to the field of medical technology and, more particularly, to devices, systems, and methods for assessing flow at an anatomical region of interest, including determining a blood flow measurement in a vessel, using image data.

BACKGROUND

To better understand the severity of a particular condition at an anatomical region of a patient, physiological data can be gathered and used to guide treatment decisions. One example of such a condition is a constriction, or narrowing, of a blood vessel, often referred to as a stenosis. By gauging the extent of the constriction, appropriate treatment options can be determined.

One technique for evaluating the degree to which a stenosis obstructs flow through a blood vessel is called the Fractional Flow Reserve measurement (FFR). To calculate FFR for a given stenosis, two blood pressure readings are taken—one on the distal side of the stenosis and the other on the proximal, or aortic, side of the stenosis. FFR is defined as the ratio of maximal blood flow in a stenotic artery, taken distal to the stenosis, to normal maximal blood flow, and is typically calculated based on a measured pressure gradient of the distal pressure to the proximal pressure. The pressure gradient across a stenosis is an indicator of the severity of the stenosis. The more restrictive the stenosis is, the greater the pressure drop, and the lower the resulting FFR. FFR measurement may be a useful diagnostic tool. A physician might decide, for example, to perform an interventional procedure (e.g., angioplasty or stent placement) when FFR for a given stenosis is below a clinical threshold (e.g., 0.8), and may decide to forego such treatment for a given stenosis where FFR is above the clinical threshold. Thus, FFR measurement can be a decision point for guiding treatment.

Traditionally FFR measurements have been taken using an invasive pressure measurement device. However, to avoid the use of an invasive measurement device, FFR estimates can be derived using angiographic images. To do so, a three-dimensional rendering of a vessel is created from two or more angiographic images and blood flow is estimated using the images. Generally, blood flow velocity has been estimated by counting the number of image frames, which corresponds to a known time, it takes for the leading edge of contrast media to travel through the coronary arteries. Length of the coronary arteries is then divided by this time to estimate blood flow velocity. Blood flow velocity and the vessel rendering are used as inputs in a fluid flow model to output an estimated pressure drop.

SUMMARY

While angiographic-derived FFR measurements can eliminate use of an invasive measurement device, the accuracy of previous angiographic-derived FFR measurement techniques suffer from certain inherent and variable biases. For instance, previous angiographic-derived FFR measurement methods utilize a high pressure, large volume contrast media injection that creates forced flow acting to artificially increase flow and thereby bias flow estimates. In addition, blood flow can vary throughout the cardiac cycle such that diagnostically significant variability in flow estimates can occur depending on injection timing relative to the cardiac cycle. Such accuracy issues associated with these previous angiographic-derived FFR measurements may tend to outweigh their advantage of being minimally invasive. These accuracy issues have hindered the value of previous angiographic-derived FFR measurements.

Exemplary embodiments are described herein for measuring flow at an anatomical region of interest. Various embodiments described herein can provide a reliable, accurate, and minimally invasive flow measurement derived from image data. In particular, various embodiments disclosed herein can increase the accuracy of minimally invasive, angiographic-derived FFR measurements by reducing or eliminating the inherent and variable biases that detrimentally impact previous angiographic-derived FFR techniques. For instance, certain embodiments disclosed herein can reduce or eliminate the impact forced flow within the region of interest has on artificially increasing flow and/or the variability caused by the different phases of the cardiac cycle. Some embodiments can utilize pulsed, timed and known contrast media injections to improve the consistency and accuracy of frame counting techniques for estimating flow velocity. In addition, certain further embodiments can synchronize injection timing with a particular phase of the cardiac cycle so that data used in estimating flow better approximates a native blood flow (e.g., blood flow when no injection is being performed) at the region of interest.

One exemplary embodiment includes a method for determining a blood flow velocity in a vessel. This method embodiment includes a step of injecting pulsed contrast boluses into the vessel at a known frequency by injecting a first bolus of contrast media into the vessel over a first time, terminating injection of contrast media over a second time that is after the first time, and injecting a second bolus of contrast media into the vessel over a third time that is after the second time. This method embodiment further includes a step of analyzing image data representing a first region of the vessel to determine a distance between the first bolus of contrast media and the second bolus of contrast media in the vessel. And, this method embodiment can include a step of calculating the blood flow velocity for the first region of the vessel by multiplying the determined distance between the first bolus of contrast media and the second bolus of contrast media by the known frequency.

Another exemplary embodiment includes a non-transitory computer-readable storage article having computer-executable instructions stored thereon to cause at least one programmable processor to analyze image data representing a first region of a vessel to determine a distance between a first bolus of contrast media and a second bolus of contrast media in the vessel. This article embodiment also has computer-executable instructions stored thereon to cause at least the one programmable processor to calculate a blood flow velocity for the first region of the vessel by multiplying the determined distance between the first bolus of contrast media and the second bolus of contrast media by a known frequency at which pulsed contrast boluses, including at least the first bolus of contrast media and the second bolus of contrast media, are injected into the vessel over a first time.

An additional exemplary embodiment includes a method for determining a blood flow rate in a vessel. This method embodiment includes a step of injecting contrast media into the vessel at a first contrast injection flow rate. This method embodiment further includes a step of analyzing first image data representing a first region of interest acquired at a first acquisition time to determine if the first contrast injection flow rate has caused a predetermined condition to be present in the first image data. This method embodiment also includes a step of injecting contrast media into the vessel at a second contrast injection flow rate that is greater than the first contrast injection flow rate. Furthermore, this method embodiment includes a step of analyzing second image data representing the first region of interest acquired at a second acquisition time to determine if the second contrast injection flow rate has caused the predetermined condition to be present in the second image data. And, upon determining that the predetermined condition is present in the second image data, this method embodiment includes a step of using the second contrast injection flow rate to determine the blood flow rate in the vessel.

A further exemplary embodiment includes a non-transitory computer-readable storage article having computer-executable instructions stored thereon to cause at least one programmable processor to analyze first image data representing a first region of interest acquired at a first acquisition time to determine if a first contrast injection flow rate at which contrast media was injected into a vessel has caused a predetermined condition to be present in the first image data. This article embodiment also has computer-executable instructions stored thereon to cause at least the one programmable processor to analyze second image data representing the first region of interest acquired at a second acquisition time to determine if a second contrast injection flow rate at which contrast media was injected into the vessel and which is greater than the first contrast injection flow rate has caused the predetermined condition to be present in the second image data. And, this article embodiment also has computer-executable instructions stored thereon to cause at least the one programmable processor to, upon determining that the predetermined condition is present in the second image data, use the second contrast injection flow rate to determine a blood flow rate in the vessel.

Another exemplary embodiment includes a method for determining a blood flow measurement in a vessel. This method embodiment includes a step of performing a first injection of a contrast media into the vessel during either the systolic phase or the diastolic phase of a cardiac cycle. This method embodiment further includes a step of terminating the first injection of the contrast media. After terminating the first injection, this method embodiment includes a step of calculating the blood flow measurement for a first region of the vessel based on image data representing the contrast media at the first region. In certain embodiments, the first injection of the contrast media is terminated prior to the beginning of the other of the systolic phase and the diastolic phase of the cardiac cycle. In other embodiments, the first injection of the contrast media is terminated after one or more subsequent phases of the cardiac cycle.

An additional exemplary embodiment includes a non-transitory computer-readable storage article having computer-executable instructions stored thereon to cause at least one programmable processor to calculate a blood flow measurement for a first region of a vessel based on image data representing injected contrast media at the first region. In this article embodiment, computer-executable instructions stored thereon cause at least the one programmable processor to base the blood flow measurement calculation on image data representing contrast media injected into the vessel during one of a systolic phase and a diastolic phase of a cardiac cycle and terminated at a specific point. In some embodiments, that termination point may be prior to the beginning of the other of the systolic phase and diastolic phase of the cardiac cycle. In some embodiments, that termination point may be after one or more subsequent phases of the cardiac cycle.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

FIG. 3A shows the region of the vessel at a first image data acquisition time and FIG. 3B shows the region of the vessel at a second image data acquisition time.

FIGS. 5A-5D are schematic diagrams representing a region of vessel and showing a sequence that illustrates a relative comparison of injected contrast flow to blood flow at the region of the vessel.

DETAILED DESCRIPTION

The following detailed description is exemplary in nature and provides some practical illustrations and examples. Those skilled in the art will recognize that many of the noted examples have a variety of suitable alternatives.

A number of various exemplary flow measurement techniques are disclosed herein using the description provided as follows in addition to the accompanying drawings. Each of the techniques disclosed herein can, in some examples, be employed independently or in combination with one or more (e.g., all) of the other techniques disclosed herein.

Figure 1:
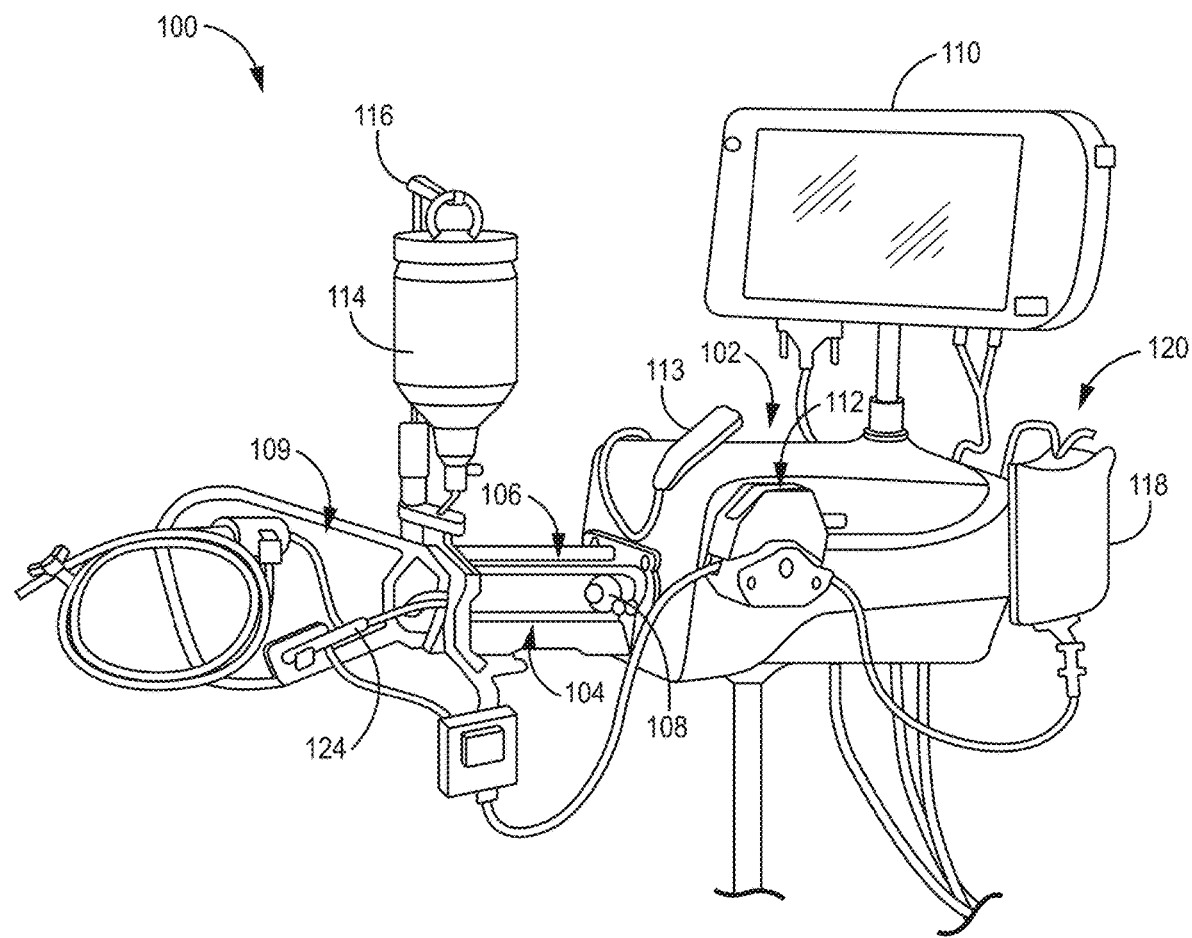
FIG. 1 is a perspective view of an embodiment of a powered fluid injector.

FIG. 1 illustrates a perspective view of an exemplary embodiment of a powered fluid injector 100. In operation, the powered fluid injector 100 can inject a quantity of fluid into a patient, for instance into a vessel of a patient via a catheter. The fluid injected by the powered fluid injector 100 can be, for example, a contrast fluid, a non-contrast fluid (e.g., saline), or a combination thereof. By injecting a quantity of fluid into a patient, the powered fluid injector 100 can facilitate a variety of medical diagnostic and/or interventional procedures, including the collection of image data representing an anatomical region of interest. These procedures can include, as examples, optical coherence tomography (OCT) imaging, intravascular ultrasound (IVUS) imaging, computed tomography (CT) imaging, magnetic resonance (MRI) imaging, angiographic procedures, and interventional device procedures/placements.

The illustrated powered fluid injector 100 includes a drive assembly housing 102 and a sleeve 104. The sleeve 104 can be secured to the drive assembly housing 102. For example, the drive assembly housing 102 can include an opening and the sleeve 104 can be secured to the drive assembly housing 102 at or near such opening. The sleeve 104 may extend out from the drive assembly housing 102 and may be configured to receive and hold a reservoir 106. The reservoir 106 can have an internal reservoir volume containing a fluid and include a plunger 108 within the internal reservoir volume. At least a portion of a drive assembly can be housed within the drive assembly housing 102. The drive assembly can be configured to pressurize fluid within the internal reservoir volume. For instance, the drive assembly may couple to the plunger 108, such as at the opening in the drive assembly housing 102, and drive the plunger 108 within the internal reservoir volume. As the plunger 108 is progressively driven within the reservoir 106, fluid within the internal reservoir volume can be pressurized and output from the reservoir 106 along tubing 109 leading to a patient. In certain applications of the powered fluid injector 100, output fluid, such as contrast media, can be pressurized anywhere from 1000-1500 psi (e.g., 1200 psi).

The illustrated embodiment of the powered fluid injector 100 includes several features that can be useful in pressurizing and delivering fluid during operation. The powered fluid injector 100 can include a control panel 110. The control panel 110 can provide a user interface for various operational aspects. For example, the control panel 110 can be utilized by an operator to set up various parameters and/or protocols to be used for a given fluid injection procedure. In one example, the operator can interact with the control panel 110 to input fluid injection parameters such as flow rate, injection volume (e.g., maximum), injection pressure (e.g., maximum), fluid injection duration, rise time, and/or other injection parameters. In one embodiment, control panel 110 includes a touch-screen panel display, enabling an operator to view and modify injection parameters. The control panel 110 can also be used to initialize powered fluid injector 100 (e.g., to prepare it for a patient fluid injection), or to activate certain features or sequences of operation. The control panel 110 may also provide status information, including information related to past or currently ongoing injection procedures as well as any appropriate alerts. The control panel 110 can include an imaging engine having one or more processors from controlling operation of the powered fluid injector 100. Such processors can also control other components, such as the drive assembly, a peristaltic pump 112, when present, and/or any sensors and detectors included at the powered fluid injector 100.

In addition to the control panel 110, the illustrated powered fluid injector 100 includes a hand-control device 113 for operator input. The hand-control device 113 can be coupled to the control panel 110 either wirelessly or via a lined connection. Although, in other embodiments, the hand-control device 113 can be connected to a component of powered fluid injector 100 other than control panel 110, such as drive assembly housing 102. The hand-control device 113 can generate and send various signals related to an injection procedure to the control panel 110 or other connected component. An operator can actuate one or more interface components at the hand-control device 113 to control an injection procedure. For example, the operator can use hand-control device 113 as a variable-rate control device to alter the fluid flow rate output from the powered fluid injector 100 and/or as a mechanism for starting or stopping a fluid injection.

The powered fluid injector 100 can also include one or more components useful for supplying fluid to be used in an injection procedure. A container 114 can include a supply of fluid, such as contrast media, and be secured to a holder 116 at the powered fluid injector 100. Fluid from the container 114 can be supplied to the reservoir 106 for use during an injection procedure. For example, fluid from the container 114 can be drawn into the reservoir 106 when the plunger 108 is being retracted (e.g., moved in a direction toward the drive assembly housing 102) and thereby refill the internal reservoir volume. Similarly, when the powered fluid injector 100 includes the peristaltic pump 112, a second container 118 can include a supply of fluid, such as a flushing medium (e.g., saline), and be secured to a holder 120 at the powered fluid injector 100. When present, the peristaltic pump 112 can receive fluid from the second container 118 and deliver such fluid to the patient. Often times, the peristaltic pump 112 may be used to deliver non-contrast fluid, such as saline, at a lower pressure than that at which the drive assembly delivers contrast fluid from the reservoir 106. A valving system 124 can be included to selectively place the reservoir 106 or peristaltic pump 112 in communication with the patient.

Figure 2:
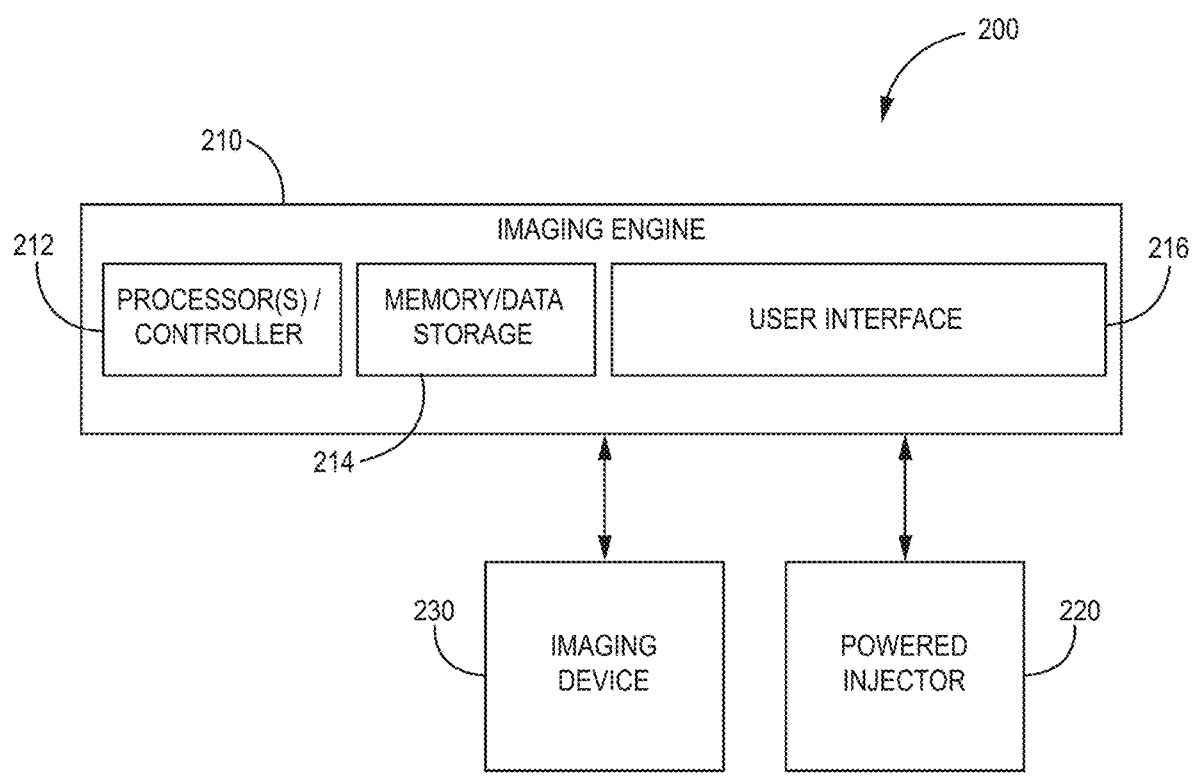
FIG. 2 is a block diagram of an embodiment of a system configured to generate and analyze image data representing an anatomical region of interest.

FIG. 2 is a block diagram illustrating an exemplary system 200 configured to generate and analyze image data representing an anatomical region of interest. As shown in this example, the system 200 can include an imaging engine 210, a powered fluid injector 220, and an imaging device 230.

In this embodiment, the imaging engine 210 is shown to be in communication with the powered fluid injector 220 and the imaging device 230. In this way, the imaging engine 210 can communicate with the powered fluid injector 220 and the imaging device 230. For example, the imaging engine 210 can receive data from the powered fluid injector 220, such as fluid injection parameters including flow rate, injection duration (e.g., injection start time, injection end time), injection frequency, and injection volume. The imaging engine 210 can also receive data from the imaging device 230, such as one or more frames of image data representing an anatomical region of interest.

The imaging engine 210 can analyze data received from the powered fluid injector 220 and/or the imaging device 230. The imaging engine 210, in the illustrated example, includes one or more programmable processors 212, memory/data storage component 214 which can be in communication with the one or more programmable processors 212, and a user interface 216 which can be in communication with the one or more programmable processors 212 and/or the memory/data storage component 214. Data received from the powered fluid injector 220 and/or the imaging device 230 can be analyzed at the imaging engine 210 and output onto the user interface 216. For example, the memory/data storage component 214 can include a non-transitory computer-readable storage article having computer-executable instructions stored thereon and executable by at least one programmable processor 212 to perform one or more analyses described further herein based on the image data and also, in some cases, based on the one or more injection parameters. The user interface 216 can include a display for outputting a measurement calculated according to the computer-executable instructions.

The powered fluid injector 220 can be the same as, or similar to, the powered fluid injector disclosed in reference to FIG. 1 and, as noted, can be in communication with the imaging engine 210. In some examples, the powered fluid injector 220 can be controlled by the imaging engine 210. For example, the imaging engine 210 can provide one or more signals to the powered fluid injector 220 relating to one or more injector parameters. In one example, the imaging engine 210 can send one or more signals to the powered fluid injector 220 to start a first fluid (e.g., contrast) injection at a specified flow rate and to stop the first fluid injection after a predefined injection duration. In a further example, the one or more signals from the imaging engine 210 to the powered fluid injector 220 can further command the powered fluid injector 220 to start a second fluid injection (e.g., of the same or different fluid as the first injection) at a specified flow rate (e.g. the same flow rate as the first injection, an increased flow rate from the first injection, a decreased flow rate from the first injection) a predefined time period after termination of the first fluid injection. In this way, the powered fluid injector 220 can perform multiple fluid injections at one or more specified flow rates and/or at a specified frequency.

The imaging device 230 can be any one or more types of imaging apparatuses suitable for collecting image data as appropriate for a particular application. For example, the imaging device 230 can be an optical coherence tomography (OCT) imaging module, intravascular ultrasound (IVUS) imaging module, computed tomography (CT) imaging module, magnetic resonance (MRI) imaging module, or X-ray imaging module. In one application, the imaging device 230 can include an imaging module, such as an X-ray, suitable for generating one or more frames of angiographic image data of a patient. In such an application, angiographic image data can represent one or more vessels of a vascular system and one or more organs of a patient. Such image data can be useful for assessing blood flow through vessel lumens of the patient. When contrast media is injected into the vessel, blood may be temporarily displaced from a portion of the vessel lumen by this injected contrast media and the injected contrast media can facilitate collection of image data representing one or more vessels and/or other region of interest.

As will now be described further herein, image data representing one or more regions of the vessel, and/or other anatomical region of interest, can be used to assess blood flow. For example, various embodiments disclosed herein can use such image data to derive a reliable, accurate, and minimally invasive blood flow measurement, such as a blood flow velocity or blood volumetric flow rate, pertaining to the vessel and/or other anatomical region of interest. In some embodiments, blood flow velocity can be measured, and the measurement can be converted to blood volumetric flow rate. In some embodiments, blood volumetric flow rate can be measured, and the measurement can be converted to blood flow velocity. The remaining disclosure that follows describes a number of particular exemplary embodiments for measuring flow at a region of interest using image data.

Some embodiments can determine a blood flow velocity by analyzing image data representing a region of interest having a number of pulsed contrast boluses injected at a known frequency. In general, a contrast media injection frequency can be set (e.g., at the powered fluid injector) and used in conjunction with image data representing a region of interest having the contrast media injected at a known frequency to derive a flow velocity for that region of interest. In this way, a known contrast media injection frequency can serve as a means to ultimately derive a flow velocity. Moreover, in embodiments where the contrast media injection frequency is set so as to introduce, into the region of interest, relatively small contrast media boluses over short injection durations the impact of forced flow that can otherwise result from relatively more prolonged contrast media injection can be minimized. And, in this way, such flow measurement techniques utilizing frequency modulated contrast media injections may be able to facilitate more accurate flow measurement.

Figure 3A:
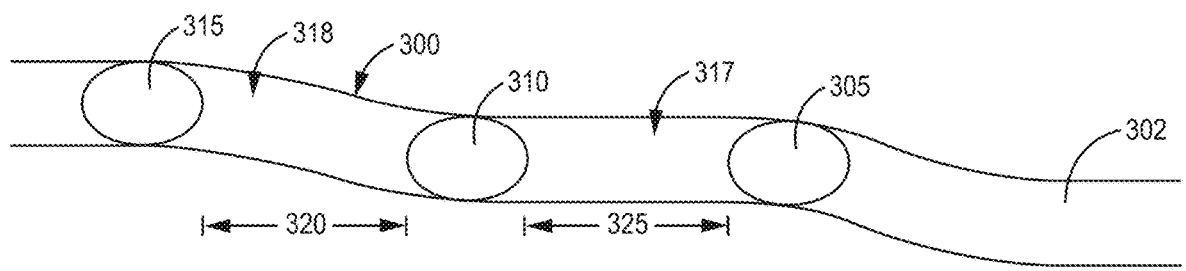
FIGS. 3A and 3B are schematic diagrams representing a region of a vessel including pulsed contrast boluses.
Figure 3B:
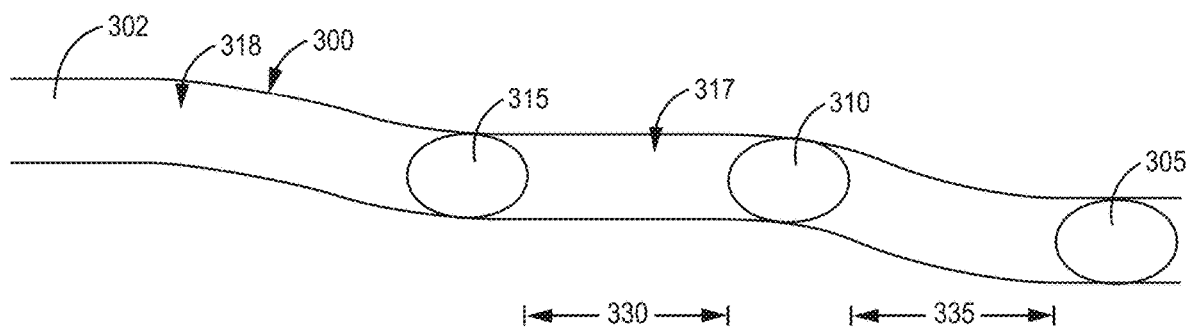
Figure 4:
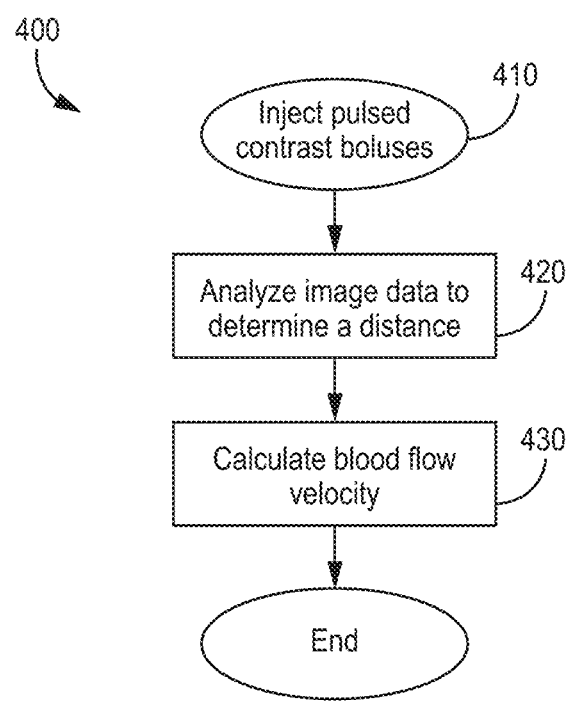
FIG. 4 is a flow diagram of an embodiment of a method for determining a blood flow velocity in a region of interest using pulsed contrast boluses.

Referring to FIGS. 3A, 3B, and 4, some embodiments, as noted, can determine a blood flow velocity by analyzing image data representing a region of interest having a number of pulsed contrast boluses injected at a known frequency. In particular, FIGS. 3A and 3B are schematic diagrams representing a region of a vessel including pulsed contrast boluses. FIG. 3A shows the region of the vessel at a first image data acquisition time and FIG. 3B shows the region of the vessel at a second image data acquisition time. FIG. 4 shows a flow diagram of an embodiment of a method 400 for determining a blood flow velocity in a region of interest using image data representing a number of such pulsed contrast boluses at the region of interest.

FIG. 3A shows a region of a vessel 300. While the example here shows the region of interest as including the portion of the vessel 300, in other examples the region of interest can include multiple vessels and/or one or more other anatomical regions depending on the particular application. For instance, while the details described herein can be applicable to a wide variety of anatomical regions, in one example the vessel 300 can be a coronary artery. The vessel 300 defines a lumen 302. A number of boluses of contrast media can be present within the lumen 302, including as shown here a first bolus of contrast media 305, a second bolus of contrast media 310, and a third bolus of contrast media 315.

These contrast boluses 305, 310, 315 can be injected into the vessel 300 at a known frequency to create a discreet number of pulsed contrast boluses. For instance, a powered fluid injector can be used to inject the contrast boluses 305, 310, 315 into the vessel 300 at a known frequency. Namely, the frequency at which the contrast boluses 305, 310, 315 are injected into the vessel 300 can be set at the powered fluid injector such that contrast media is injected for a predetermined duration every predetermined interval of time. The known frequency can define the predetermined interval of time between contrast injections (e.g., the time over which contrast injection is terminated). For example, the first bolus of contrast media 305 can be injected into the vessel 300 over a first time. Then injection of contrast media can be terminated over a second time that is after the first time. The second bolus of contrast media 310 can then be injected into the vessel 300 over a third time that is after the second time. Then injection of contrast media can be terminated over a fourth time that is after the third time. In some embodiments this process can be repeated so as to create additional pulsed contrast boluses within the vessel 300. For instance, as shown here, the third bolus of contrast media 315 can then be injected into the vessel 300 over a fifth time that is after the fourth time. In many cases, the duration of each contrast media injection (e.g., the first time, the third time, and the fifth time) can be equal or substantially equal and the time between contrast media injections (e.g., the second time and the fourth time) can be equal or substantially equal.

The injector can inject contrast boluses 305, 310, 315 into the vessel 300 according to a variety of parameters. In some embodiments, the injector can inject contrast boluses 305, 310, 315 into the vessel 300 at a particular frequency. In some examples, the frequency may be between 1 Hz (the start of each injection occurs 1 second after the last one started) and 50 Hz. In some examples, the frequency may be between 5 Hz and 20 Hz. In some embodiments, the injector can inject contrast boluses 305, 310, 315 into the vessel 300 according to a duty cycle. The injector can inject contrast media for a first time and then not inject contrast media for a second time. The duty cycle can be the percentage of the first time compared to the total of the first time and the second time. In some examples, the duty cycle may be between 5% (from the start of one injection to the start of the next injection, contrast media is injected for 5% of the time) and 75%. In some embodiments, the duty cycle may be between 10% and 50%. In an example of a 1 Hz frequency and a 10% duty cycle, injector can inject contrast media for 100 milliseconds and not inject contrast media for 900 milliseconds in a repeated pattern.

In one case, pulsed contrast boluses can be created by alternating injection of contrast media with injection of saline such that alternating packets of contrast and saline are introduced into the vessel 300. For instance, in the injection sequence example described above, saline fluid can be injected into the vessel 300 over the second time when the contrast injection is terminated such that saline fluid is present in the vessel 300 between the first bolus of contrast media 305 and the second bolus of contrast media 310. Likewise, in the injection sequence example described above, saline fluid can be injected into the vessel 300 over the fourth time when the contrast injection is terminated such that saline fluid is present in the vessel 300 between the second bolus of contrast media 310 and the third bolus of contrast media 315.

In another case, pulsed contrast boluses can be created by alternately starting and stopping injections of contrast media such that alternating packets of contrast media boluses and blood are created in the vessel 300. For instance, in the injection sequence example described above, no fluid may be introduced into the vessel 300 over the second time when the contrast injection is terminated such that blood is present in the vessel 300 between the first bolus of contrast media 305 and the second bolus of contrast media 310. Likewise, in the injection sequence example described above, no fluid may be introduced into the vessel 300 over the fourth time when the contrast injection is terminated such that blood is present in the vessel 300 between the second bolus of contrast media 310 and the third bolus of contrast media 315.

As two or more contrast media boluses 305, 310, 315 have been created using the know injection frequency, image data can be generated and analyzed. FIG. 3A shows the vessel 300 at a first image data acquisition time. At the first acquisition time, image data that includes one or more regions of the vessel 300 can be generated by an appropriate imaging device. For instance, in one example, the image data can be angiographic image data. In certain embodiments, the image data representing one or more regions of the vessel can be a single frame of image data. For instance, if image data representing the vessel 300 is acquired at both a first image data acquisition time and a later, second image data acquisition time, the image data acquired at each time can be a single frame of image data of the vessel 300. In some cases, the first image data acquisition time can be after the second bolus of contrast media 310 has been injected into the vessel 300. The second image data acquisition time can be after the first image data acquisition time, including in some cases after the third bolus of contrast media 315 has been injected into the vessel 300.

Image data representing the vessel 300 can be analyzed to ascertain the position of the two or more contrast media boluses 305, 310, 315 in the vessel 300. In some embodiments, the image data representing the vessel 300 can be analyzed for peak pixel density to determine a position of the two or more contrast media boluses 305, 310, 315 in the vessel 300. This can include using one or more predetermined peak pixel density values for determining whether a particular location in the vessel 300 represented in the image data includes a contrast media bolus.

For example, image data representing a first region 317 of the vessel 300 at the first image acquisition time, shown in FIG. 3A, can be analyzed to determine a distance 325 between the first bolus of contrast media 305 and the second bolus of contrast media 310. As noted, in some embodiments, this analysis can include analyzing peak pixel density of the image data representing the first region 317 of the vessel 300 to determine a position of the first bolus of contrast media 305 in the first region 317 and a position of the second bolus of contrast media 310 in the first region 317. The distance 325 between the two contrast boluses 305, 310 can be measured using a variety of reference points associated with each contrast bolus 305, 310. For instance, the example shown in FIG. 3A shows the distance 325 measured from a trailing portion (e.g., upstream portion relative to fluid flow direction) of the first bolus of contrast media 305 to a leading portion (e.g., downstream portion relative to fluid flow direction) of the second bolus of contrast media 310. In another example, a center point of each bolus 305, 310 can be used as a reference point for measuring the distance 325.

Once the distance 325 between the first bolus of contrast media 305 and the second bolus of contrast media 310 has been determined, a flow velocity for first region 317 of the vessel 300 can be calculated. To calculate the flow velocity for the first region 317, the determined distance 325 between the first bolus of contrast media 305 and the second bolus of contrast media 310 can be multiplied by the known frequency at which the contrast boluses were injected into the vessel 300. This calculated flow velocity can be used as a measure of the blood flow velocity at the first region 317 of the vessel 300.

In some embodiments, it may be useful to calculate a flow velocity for two or more different anatomical regions. As one example, a flow velocity for a second region 318 of the vessel 300 can be calculated in addition to a flow velocity for the first region 317 of the vessel 300. As shown in the illustrated example, the second region 318 can be upstream of the first region 317 in the vessel 300. In other examples, flow velocities for different vessels and/or other different anatomical regions can be calculated using the techniques disclosed herein.

Similar to that described with respect to the first region 317, image data representing a second region 318 of the vessel 300 at the first image acquisition time, shown in FIG. 3A, can be analyzed to determine a distance 320 between the second bolus of contrast media 310 and the third bolus of contrast media 315. As noted, in some embodiments, this analysis can include analyzing peak pixel density of the image data representing the second region 318 of the vessel 300 to determine a position of the second bolus of contrast media 310 in the second region 318 and a position of the third bolus of contrast media 315 in the second region 318. As with the distance 325 for the first region 317, the distance 320 between the two contrast boluses 310, 315 can be measured using a variety of reference points associated with each contrast bolus 310, 315. It may in some cases be beneficial to measure the distance 325 and the distance 320 using the same reference point associated with each bolus 305, 310, 315.

Once the distance 320 between the second bolus of contrast media 310 and the third bolus of contrast media 315 has been determined, a flow velocity for second region 318 of the vessel 300 can be calculated. To calculate the flow velocity for the second region 318, the determined distance 320 between the second bolus of contrast media 310 and the third bolus of contrast media 315 can be multiplied by the known frequency at which the contrast boluses were injected into the vessel 300. This calculated flow velocity can be used as a measure of the blood flow velocity at the second region 318 of the vessel 300.

Calculating blood flow velocities for two or more different anatomical regions can be useful in providing a relative flow assessment at the particular anatomical location. For example, a calculated blood flow velocity for one region can be compared to a calculated blood flow velocity for a different region to determine whether a diagnostically significant flow difference is present at the particular anatomical location. For instance, with respect to the vessel 300, the calculated blood flow velocity for the first region 317 can be compared to the calculated blood flow velocity for the second region 318 to determine whether a difference between the calculated blood flow velocity for the first region 317 and the calculated blood flow velocity for the second region 318 exceeds a predetermined flow velocity differential threshold. In some applications, the difference between the calculated blood flow velocity for the first region 317 and the calculated blood flow velocity for the second region 318 exceeding the predetermined flow velocity differential threshold can indicate diagnostically useful information. As one example, this may indicate that the vessel 300 includes a constriction (e.g., a stenosis).

In some further embodiments, analyzing image data acquired at different acquisition times may be useful in increasing the accuracy of the flow velocity calculation. For example, the distance between the first bolus of contrast media 305 and the second bolus of contrast media 310 may be determined with greater accuracy by using distances between the first bolus of contrast media 305 and the second bolus of contrast media 310 represented in image data acquired at different image data acquisition times. The same can be true for determining the distance between the second bolus of contrast media 310 and the third bolus of contrast media 315.

FIG. 3B again shows the vessel 300 but at a second image data acquisition time that is after the first image data acquisition time represented in FIG. 3A. As can be seen in FIG. 3B, each bolus 305, 310, 315 has moved downstream in the vessel 300 from their respective locations in the vessel 300 at the first image data acquisition time.

In one example, the image data representing the first region 317 includes a first frame of image data representing the first region 317 acquired at a first acquisition time (e.g., as shown in FIG. 3A) and a second frame of image data representing the first region 317 acquired at a second acquisition time (e.g., as shown in FIG. 3B). In this example, the first frame of image data representing the first region 317 of the vessel 300 at the first image acquisition time, shown in FIG. 3A, can be analyzed to determine the distance 325 between the first bolus of contrast media 305 and the second bolus of contrast media 310 in the first frame of image data. In addition, the second frame of image data representing the first region 317 of the vessel 300 at the second image acquisition time, shown in FIG. 3B, can be analyzed to determine a distance 335 between the first bolus of contrast media 305 and the second bolus of contrast media 310 in the second frame of image data. The distance 325 and the distance 335 can be combined and then multiplied by the known frequency at which the contrast boluses were injected into the vessel 300 to calculate a flow velocity for the first region 317 of the vessel 300. For instance, the distance 325 and the distance 335 can be combined by averaging the distance 325 and the distance 335. The use of multiple distance measurements in calculating the flow velocity for an anatomical region may be useful in providing a larger data set from which the calculation is made thereby acting to increase accuracy of the calculation.

Likewise, in certain further embodiments, the image data representing the second region 318 includes a first frame of image data representing the second region 318 acquired at a first acquisition time (e.g., as shown in FIG. 3A) and a second frame of image data representing the second region 318 acquired at a second acquisition time (e.g., as shown in FIG. 3B). In this example, the first frame of image data representing the second region 318 of the vessel 300 at the first image acquisition time, shown in FIG. 3A, can be analyzed to determine the distance 320 between the second bolus of contrast media 310 and the third bolus of contrast media 315 in the first frame of image data. In addition, the second frame of image data representing the second region 318 of the vessel 300 at the second image acquisition time, shown in FIG. 3B, can be analyzed to determine a distance 330 between the second bolus of contrast media 310 and the third bolus of contrast media 315 in the second frame of image data. The distance 320 and the distance 330 can be combined and then multiplied by the known frequency at which the contrast boluses were injected into the vessel 300 to calculate a flow velocity for the first region 317 of the vessel 300. As noted above, for instance, the distance 320 and the distance 330 can be combined by averaging the distance 320 and the distance 330.

Embodiments that determine a blood flow velocity by analyzing image data representing a region of interest having a number of pulsed contrast boluses injected at a known frequency can be useful in providing an accurate and minimally invasive measurement. For instance, by injecting relatively short, dense packets of contrast media, the impact on natural blood flow in the region of interest can be minimized and flow velocity can be estimated at any point along the region of interest (e.g., the coronary artery). With this estimated flow velocity, a flow map of all of, or a portion of, a coronary tree may be created using one or more (e.g., a single) angiographic image. When used in a coronary artery application, this technique can improve on prior techniques that rely on assumptions when determining coronary side branch flow. In this way, each image frame can be processed individually to provide a detailed flow profile during a full cardiac cycle. Furthermore, in some embodiments to further increase accuracy, multiple image frames can be averaged and then the average across frames can be used to derive flow velocity.

As noted, FIG. 4 shows a flow diagram of an embodiment of a method 400 for determining a blood flow velocity in a region of interest by analyzing image data representing the region of interest having a number of pulsed contrast boluses injected at a known frequency. In various embodiments of the method 400, one or more of the details provided above in reference to FIGS. 3A and 3B can be implemented at the corresponding step in the method 400.

At step 410 in the method 400, pulsed contrast boluses are injected into the vessel at a known frequency. Pulsed contrast boluses can be injected into the vessel at a known frequency by injecting a first bolus of contrast media into the vessel over a first time, terminating injection of contrast media over a second time that is after the first time, and injecting a second bolus of contrast media into the vessel over a third time that is after the second time.

At step 420 in the method 400, image data representing a first region of the vessel is analyzed. The image data representing the first region of the vessel can be analyzed to determine a distance between the first bolus of contrast media and the second bolus of contrast media in the vessel. Analyzing image data representing the first region of the vessel can include analyzing peak pixel density of the image data representing the first region of the vessel to determine a position of the first bolus of contrast media in the first region of the vessel and a position of the second bolus of contrast media in the first region of the vessel. In some further embodiments, image data representing a second, different region of the vessel can also be analyzed. The image data representing the second region of the vessel can be analyzed to determine a distance between the second bolus of contrast media and a third bolus of contrast media in the vessel.

At step 430 in the method 400, the blood flow velocity for the first region of the vessel is calculated. This blood flow velocity can be calculated by multiplying the determined distance between the first bolus of contrast media and the second bolus of contrast media by the known contrast media injection frequency. And, in some further embodiments, the blood flow velocity for the second region of the vessel is also calculated. This blood flow velocity can be calculated by multiplying the determined distance between the second bolus of contrast media and the third bolus of contrast media by the known contrast media injection frequency.

Non-transitory computer-readable storage article embodiments can also be used for determining a blood flow velocity in a region of interest by analyzing image data representing the region of interest having a number of pulsed contrast boluses injected at a known frequency. In various embodiments of such a non-transitory computer-readable storage article, one or more of the details provided above in reference to FIGS. 3A and 3B can be implemented in computer-executable instructions stored on the non-transitory computer-readable storage article.

For example, one such embodiment can include a non-transitory computer-readable storage article having computer-executable instructions stored thereon to cause at least one programmable processor to analyze image data representing a first region of a vessel to determine a distance between a first bolus of contrast media and a second bolus of contrast media in the vessel. For instance, in some cases the computer-executable instructions can process the image data to determine peak pixel density values corresponding to a position of one or more contrast boluses. This embodiment can also have computer-executable instructions stored thereon to cause at least the one programmable processor to calculate a blood flow velocity for the first region of the vessel by multiplying the determined distance between the first bolus of contrast media and the second bolus of contrast media by a known frequency at which pulsed contrast boluses, including at least the first bolus of contrast media and the second bolus of contrast media, are injected into the vessel over a first time. One or more other features disclosed above in reference to FIGS. 3A and 3B can also be incorporated into this particular non-transitory computer-readable storage article embodiment or other non-transitory computer-readable storage article embodiments.

Other embodiments can determine a blood flow rate for a region of interest by analyzing image data to determine when a contrast injection flow rate has caused a predetermined condition at the region of interest. In general, a contrast media injection flow rate can be set (e.g., at the powered fluid injector) and image data can be acquired at the set contrast media injection flow rate. This image data can be analyzed to determine whether the predetermined condition is present at the region of interest. If it is determined that the predetermined condition is not present, then the contrast media injection flow rate can be adjusted (e.g., increased) and image data can be acquired at the adjusted contrast media injection flow rate. Again, this image data can be analyzed to determine whether the predetermined condition is present at the region of interest. Once it is determined that the predetermined condition is present, the adjusted contrast media injection flow rate can be used to determine the blood flow rate in the vessel. For instance, the blood flow rate can be determined as equal to, approximating, a predetermined amount less than, or a predetermined amount greater than the known contrast media injection flow rate.

In this way, a known contrast media injection flow rate can serve as a means to ultimately derive a flow rate for the vessel. In some cases, such a means for determining a blood flow rate in a vessel may be seen as matching the known contrast injection flow rate to the blood flow rate in the vessel. And, in this way, such flow measurement may be able to facilitate minimally invasive and accurate flow measurement.

Figure 6:
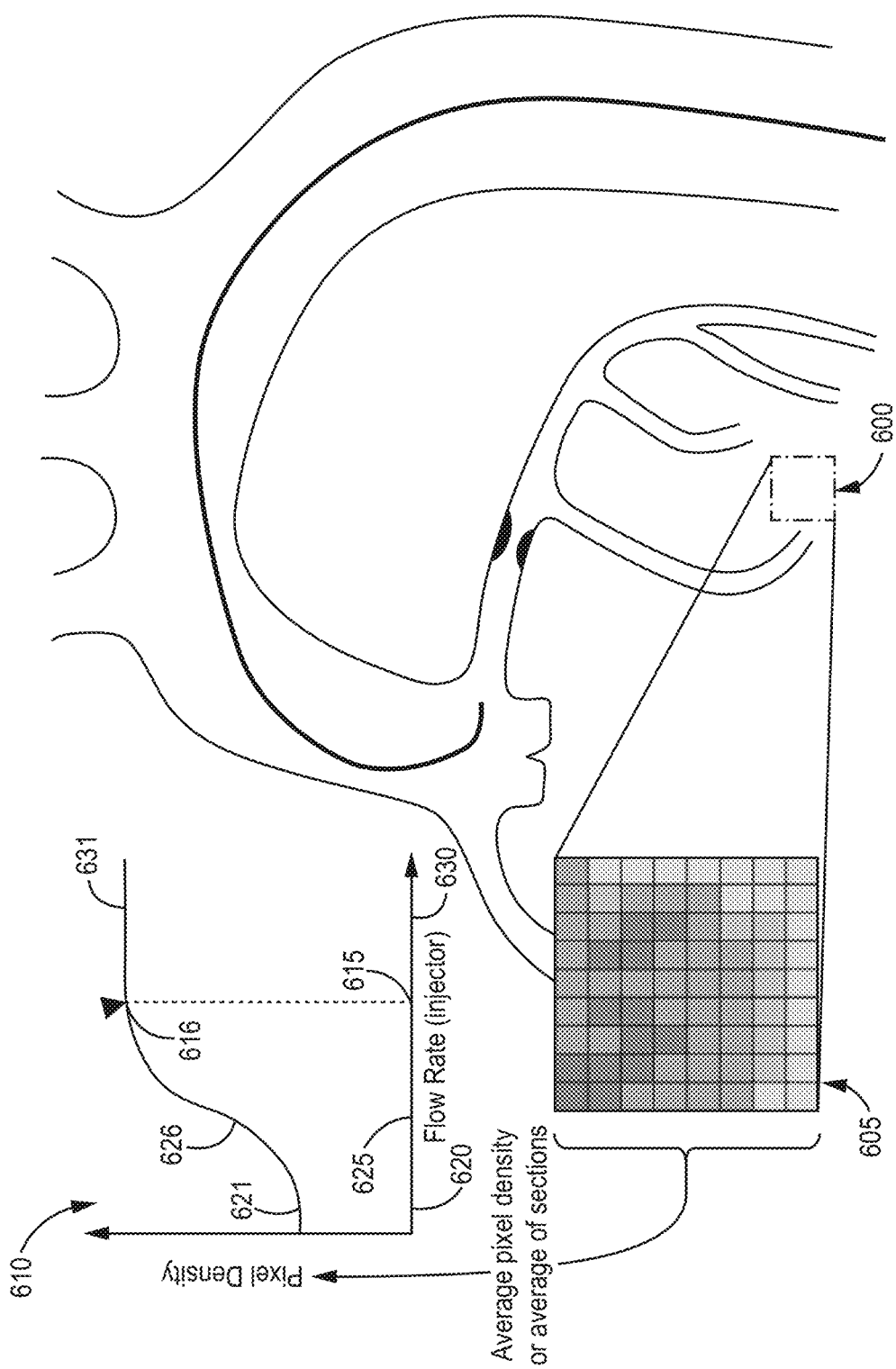
FIG. 6 is a schematic diagram of image data pixel density values for a region of interest along with associated contrast injection flow rates.
Figure 7:
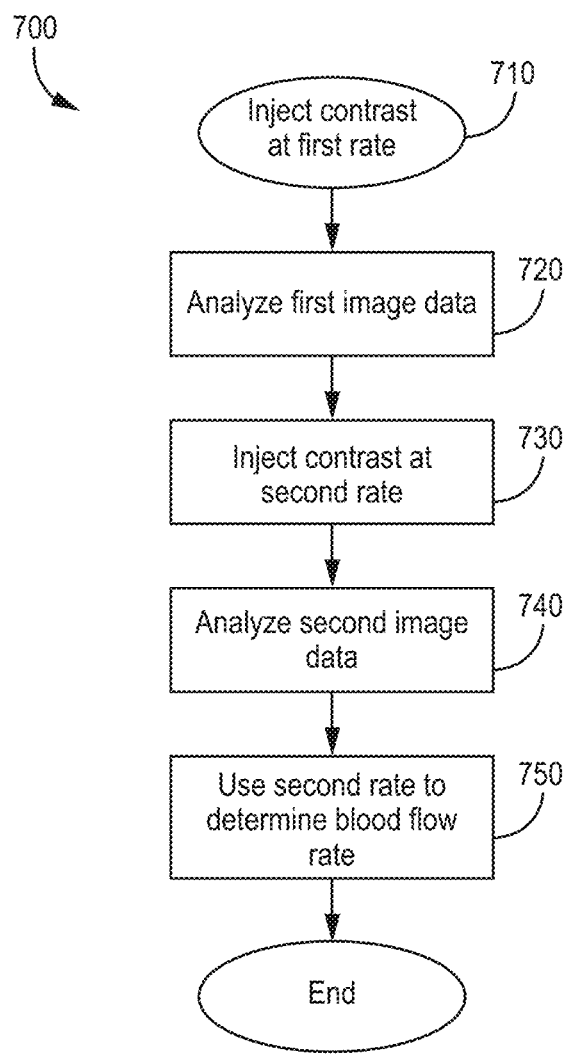
FIG. 7 is a flow diagram of an embodiment of a method for determining a blood flow rate in a region of interest using contrast injection flow rates.

Referring to FIGS. 5A-7, embodiments are shown for determining a blood flow rate in a region of interest by analyzing image data to determine when a known contrast injection flow rate has caused a predetermined condition at the region of interest. In particular, FIGS. 5A-5D are schematic diagrams representing a region of interest and show a sequence that illustrates a relative comparison of injected contrast flow to blood flow at the region of interest to determine an occurrence of one exemplary type of predetermined condition. FIG. 6 shows a schematic diagram of image data pixel density values for a region of interest along with associated contrast injection flow rates to determine an occurrence of another exemplary type of predetermined condition. And, FIG. 7 shows a flow diagram of an embodiment of a method for determining a blood flow rate in a region of interest using contrast injection flow rates.

FIGS. 5A-5D illustrate an embodiment in which the presence of contrast media flowing out from a vessel is used as one type of predetermined condition at the region of interest that results from a known contrast injection flow rate. Namely, FIGS. 5A-5D show a sequence that illustrates a relative comparison of injected contrast flow to blood flow at the region of interest to determine the presence of contrast media flowing out from a vessel. In the illustrative embodiment of FIGS. 5A-5D, a contrast injection catheter 500 may extend through the patient's aorta 502, with a catheter outlet 504 positioned in the patient's coronary artery 506. In some embodiments, the structure and technique shown in FIGS. 5A-5D may be used in one or more various other vessels, including in other anatomical regions.

In the sequence of FIGS. 5A-5D, contrast media 508 is injected into the coronary artery 506 at increasing flow rates until the flow rate gets too high, causing contrast media 508 to flow out of the coronary artery 506 back into the aorta 502. At each step, the contrast injection flow rate may be known and recorded. For example, a powered fluid injector can be used to inject the contrast media 508 so that the contrast injection flow rate can be set at a known contrast injection flow rate and controllably adjusted to other known contrast injection flow rates as desired. In FIG. 5A, contrast media injection has not yet begun, so the contrast injection flow rate is zero. In FIG. 5B, contrast media injection has begun, and contrast media 508 is being injected at a first contrast injection flow rate. The first contrast injection flow rate is less than the blood flow rate, meaning that an additional volume of contrast media 508 may be injected and flow freely within the coronary artery 506. In FIG. 5C, the contrast injection flow rate has been increased to a second contrast injection flow rate that is equal to the blood flow rate. The entire injected volume of contrast media 508 is able to flow freely within the coronary artery 506 at the second contrast injection flow rate. The contrast media 508 is flowing at the same rate as the blood within the coronary artery 506. In FIG. 5D, the contrast injection flow rate has been increased to a third contrast injection flow rate. The third contrast injection flow rate is greater than the blood flow rate. Because there is nowhere within the coronary artery 506 for the marginal volume of contrast media 510 to flow, such contrast media 510 must flow back into the aorta 502.

Image data may be acquired and analyzed at each contrast injection flow rate. At each contrast injection flow rate, the image data may be analyzed to determine if a predetermined condition is present. The predetermined condition may be the presence of contrast media 510 flowing out of the coronary artery 506 back into the aorta 502. The image data may be analyzed at each contrast injection flow rate. In the first frame in which contrast media 510 is seen flowing out of the coronary artery 506 back into the aorta 502, the corresponding contrast injection flow rate may be noted. It may then be determined that the immediately preceding contrast injection flow rate is roughly equal to the blood flow rate. In this way, the blood flow rate in the coronary artery 506 may be estimated. In some instances, the blood flow rate in the coronary artery 506 may be equal to or may approximate the contrast injection flow rate immediately preceding the contrast injection flow rate at which contrast media 510 backflow is detected. In some instances, the blood flow rate in the coronary artery 506 may be between the contrast injection flow rate at which contrast media 510 backflow is detected and the immediately preceding contrast injection flow rate.

Thus, as the exemplary sequence shown in FIGS. 5A-5D illustrates, the native flow rate of blood can be determined by matching the known contrast injection flow rate to the native flow rate of blood. Since a powered injector allows contrast media 508 to be delivered with known volumetric flow characteristics, the contrast injection flow rate can be modulated (e.g., sequentially increased) at the powered injector to observe in acquired, corresponding image data the resulting impact the contrast injection flow rate has on the flow of blood in the coronary artery 506 and/or in the aorta 502. For instance, as described, flow matching can be achieved by incrementally increasing the contrast injection flow rate until image data indicates the presence of contrast media flowing out from the coronary artery 506 back into the aorta 502. This may indicate that the native flow rate of blood is less than the known contrast injection flow rate causing this condition. For instance, the native blood flow rate can be determined as equaling, or approximating, an immediately previous, lower contrast injection flow rate. Or the native blood flow rate can be determined as being another flow rate between the contrast injection flow rate causing the condition and the immediately previous, lower contrast injection flow rate.

FIG. 6 illustrates another embodiment for determining a blood flow rate in a region of interest by analyzing image data to determine when a known contrast injection flow rate has caused a predetermined condition at the region of interest. In particular, FIG. 6 shows a schematic diagram of exemplary image data pixel density values for a region of interest along with associated contrast injection flow rates to determine a contrast injection flow rate associated with the onset of a steady state pixel density in acquired image data.

FIG. 6 illustrates a region of interest 600. The region of interest 600 can be one or more of a variety of anatomical locations depending on the particular application, and in some examples can include a myocardium or coronary vessel region of a patient. For instance, in one application the region of interest 600 may be an area of the myocardium fed by a coronary artery. Contrast media can be injected into the region of interest 600, for instance using a powered fluid injector such that the contrast injection flow rate can be set at a known flow rate and adjusted over time.

Image data 605 representing the region of interest 600 can be acquired and analyzed. In general, image data 605 can be acquired at multiple different times over a period of time, and this image data 605 can be analyzed as a contrast injection flow rate is incrementally changed (e.g., increased) over that same period of time. More particularly, in this exemplary embodiment, the image data 605 can be analyzed over the period of time to determine when a steady state pixel density in the image data 605 has been reached. The contrast injection flow rate associated with the onset of a steady state pixel density in the image data 605 can then be used to determine a blood flow rate at the region of interest 600. In some such cases, this may result in matching a known contrast injection flow rate to the onset of a steady state pixel density in the image data 605.

FIG. 6 illustrates a plot 610 that shows contrast injection flow rates versus pixel density of image data 605 representing the region of interest 600. As noted, in this embodiment the average pixel density of image data 605 is analyzed over time as the contrast injection flow rate is incrementally changed over this same time. For example, in many cases image data 605 can be acquired at a number of times, including at least one time for each contrast injection flow rate. When image data 605 includes a steady state pixel density, the associated contrast injection flow rate can be used to determine a blood flow rate for the region of interest 600. For instance, in the example shown in FIG. 6, a contrast injection flow rate 615 can be associated with the onset of a steady state pixel density of the image data 605 acquired at a time when that contrast injection flow rate was used to inject contrast media into the region of interest 600. This contrast injection flow rate 615 can then be used to determine the blood flow rate at the region of interest 600. For instance, using the contrast injection flow rate 615 to determine the blood flow rate at the region of interest 600 can include determining the blood flow rate to be equal, or substantially equal, to the contrast injection flow rate 615, determining the blood flow rate to be a preset value less than or greater than the contrast injection flow rate 615, determining the blood flow rate to be equal (or substantially equal) to a previously used contrast injection flow rate less than or greater than the contrast injection flow rate 615.

The occurrence of a steady state pixel density in the image data 605 can be determined in any one or more of a number of suitable manners. For example, each set, or frame, of image data 605 taken at a particular contrast injection flow rate can be analyzed for a pixel density value. This analysis can include, for instance, averaging a number of individual segments of each set of the image data 605 to provide one pixel density value for each set of image data 605. Then the pixel density value of each set of image data 605 taken at a particular contrast injection flow rate can be compared. An onset of steady state pixel density may be considered to occur when the pixel density values for two or more sets of image data 605 associated with respective different contrast media injection flow rates cross a predetermined pixel density threshold. For instance, a steady state pixel density may be considered to occur when the pixel density values for two or more (e.g., three, four five, etc.) sets of image data 605 associated with respective different contrast media injection flow rates are within 1%, 2%, 3%, 5%, 10%, 15%, 20%, 25%, 30%, 40%, or 50% of one another. Thus, while the occurrence of a steady state pixel density can be considered to occur when a pixel density value of two or more sets of image data 605 are equal, the occurrence of a steady state pixel density can also be considered as occurring when a pixel density value of two or more sets of image data 605 are not equal but instead within a predetermined range of one another. When a pixel density value associated with a second contrast injection flow rate differs from a pixel density value associated with a first contrast injection flow rate by more than the predetermined steady state threshold, and a pixel density value associated with a third contrast injection flow rate differs from the pixel density value associated with the second contrast injection flow rate by less than the predetermined steady state threshold, it may be determined that the onset of steady state pixel density has occurred with the second contrast injection flow rate. In some instances, such determination may be confirmed by one or more subsequent pixel density difference values being below the predetermined steady state threshold.

The plot 610 can be referred to in describing one specific example of determining a blood flow rate for the region of interest 600 using image data pixel density values for the region of interest 600 along with associated contrast injection flow rates at the region of interest 600. Contrast media can be injected into the region of interest 600 at a first contrast injection flow rate 620. First image data 605 representing the region of interest 600 can be acquired at a first acquisition time when the contrast media is being injected at the first contrast injection flow rate 620. The first image data 605 acquired at the first acquisition time can be analyzed to determine a first pixel density value 621 associated with the first image data 605. This first pixel density value 621 can then be used to determine if a steady state pixel density has occurred. In this example, as shown in the plot 610, a steady state pixel density has not occurred at the first contrast injection flow rate 620.

Contrast media can then be injected into the region of interest 600 at a second contrast injection flow rate 625. In this example the second contrast injection flow rate 625 is greater than the first contrast injection flow rate 620. Second image data 605 representing the region of interest 600 can be acquired at a second acquisition time when the contrast media is being injected at the second contrast injection flow rate 625. The second image data 605 acquired at the second acquisition time can be analyzed to determine a second pixel density value 626 associated with the second image data 605. This second pixel density value 626 can then be used to determine if a steady state pixel density has occurred. In this example, as shown in the plot 610, a steady state pixel density cannot be determined to have occurred, as the difference between the second pixel density value 626 and the first pixel density value 621 is above a predetermined steady state threshold.

Contrast media can then be injected into the region of interest 600 at a third contrast injection flow rate 615. In this example the third contrast injection flow rate 615 is greater than the second contrast injection flow rate 625. Third image data 605 representing the region of interest 600 can be acquired at a third acquisition time when the contrast media is being injected at the third contrast injection flow rate 615. The third image data 605 acquired at the third acquisition time can be analyzed to determine a third pixel density value 616 associated with the third image data 605. This third pixel density value 616 can then be used to determine if a steady state pixel density has occurred. In this example, as shown in the plot 610, a steady state pixel density cannot be determined to have occurred, as the difference between the third pixel density value 616 and the second pixel density value 626 is still above the predetermined steady state threshold.

Contrast media can then be injected into the region of interest 600 at a fourth contrast injection flow rate 630. In this example the fourth contrast injection flow rate 630 is greater than the third contrast injection flow rate 615. Fourth image data 605 representing the region of interest 600 can be acquired at a fourth acquisition time when the contrast media is being injected at the fourth contrast injection flow rate 630. The fourth image data 605 acquired at the fourth acquisition time can be analyzed to determine a fourth pixel density value 631 associated with the fourth image data 605. This fourth pixel density value 631 can then be used to determine if a steady state pixel density has occurred. In this example, as shown in the plot 610, a steady state pixel density can be determined to have occurred. The difference between the fourth pixel density value 631 and the third pixel density value 616 is below the predetermined steady state threshold. The predetermined steady state threshold was crossed between the second contrast injection flow rate 625 and the third contrast injection flow rate 615.

As such, according to this embodiment, because the third contrast injection flow rate 615 is associated with the onset of a steady state pixel density, the third contrast injection flow rate 615 can be used to determine a blood flow rate for the region of interest 600. For example, upon determining that a steady state pixel density is present within the fourth image data and that the third image data represents the onset of the steady state pixel density, the blood flow rate at the region of interest 600 can be determined to approximate the third contrast injection flow rate 615. As this particular example shows, in some cases the contrast injection flow rate at which the onset of a steady state pixel density occurs may need to be determined with reference to a greater contrast injection flow rate, which allows the steady state pixel density to be ascertainable by relative comparison to the pixel density value associated the prior, lower contrast injection flow rate.

Using the blood flow measurement embodiment described with reference to FIG. 6, the native flow rate of blood flow can be measured by matching one or more contrast injection flow rates, for example set at a powered fluid injector, to the native flow rate of blood flow at a region of interest. Since a powered injector allows contrast media to be delivered with known volumetric flow characteristics, the contrast injection flow rate can be modulated (e.g., sequentially increased) at the powered fluid injector to observe in acquired image data, representing the region of interest, the resulting impact the contrast injection flow rate has on the pixel density of the acquired image data. In certain applications, practical workflow can include selecting the area of interest, such as the myocardium fed by the coronary artery, initiating the contrast injection flow rate incrementing sequence, and recording a cine. Image data acquired at each of the different contrast injection flow rates can then be processed to determine when a steady state pixel density has occurred. The contrast injection flow rate at which the pixel density first reaches the steady state pixel density can then be used to determine a measurement of the blood flow rate in the coronary artery.

As noted, FIG. 7 shows a flow diagram of an embodiment of a method 700 for determining a blood flow rate in a region of interest using one or more contrast injection flow rates.

At step 710, contrast media is injected into a region of interest, such as a vessel, at a first contrast injection flow rate. Contrast media can be injected into the vessel using a powered fluid injector that allows the contrast injection flow rate to be set and adjusted according to known contrast injection flow rate values. In one particular case, as noted with respect to the example shown in FIGS. 5A-5D, contrast media may be injected into the coronary artery from the aorta.

At step 720, first image data representing the region of interest, such as a vessel, acquired at a first acquisition time is analyzed to determine if the first contrast injection flow rate has caused a predetermined condition to be present in the first image data. In one case the predetermined condition can be, for instance, the presence of contrast media flowing out of the coronary artery back into the aorta as described with reference to the example shown in FIGS. 5A-5D. In another case the predetermined condition can be, for instance, the onset of a steady state pixel density as described with reference to the example shown in FIG. 6. In this case, the first image data can be analyzed to determine a first pixel density value for relative comparison to other pixel density values corresponding to image data acquired at different contrast injection flow rates.

At step 730, contrast media is injected into a region of interest, such as a vessel, at a second contrast injection flow rate that is different than (e.g., greater than) the first contrast injection flow rate.

At step 740, second image data representing the region of interest, such as a vessel, acquired at a second acquisition time is analyzed to determine if the second contrast injection flow rate has caused a predetermined condition to be present in the second image data. In the case where the predetermined condition is the presence of contrast media flowing out of the coronary artery back into the aorta, the second image data can be analyzed to indicate the first incidence of contrast media flowing back into the aorta. In the case where the predetermined condition is the onset of a steady state pixel density, the second image data can be analyzed to determine a second pixel density value for relative comparison to other pixel density values, including the first pixel density value, corresponding to image data acquired at different contrast injection flow rates. In this case, the second pixel density value may be different than the first pixel density value. Also in this case, the onset of a steady state pixel density may be determined to be present in the second image data when the second pixel density value equals a steady state pixel density. For instance, this can be determined when the second pixel density value is within a predetermined range of one or more other pixel density values corresponding to image data acquired at times when different contrast injection flow rates were used. This steady state pixel density may be greater than the first pixel density value such that the first pixel density value is not within a predetermined range of the second pixel density value.

At step 750, upon determining that the predetermined condition is present in the second image data, the second contrast injection flow rate may be used to determine the blood flow rate in the region of interest, such as a vessel.

In the case where the predetermined condition is the presence of contrast media flowing out of the coronary artery back into the aorta, the second contrast injection flow rate can be used in a variety of ways to determine the blood flow rate in the region of interest. As one example, the second contrast injection flow rate can be used to determine the blood flow rate in the region of interest by determining that the blood flow rate in the vessel is less than the second contrast injection flow rate. For instance, this can include determining that the blood flow rate in the region of interest approximates the first contrast injection flow rate or is within a predetermined amount of the first contrast injection flow rate. This can instead include determining that the blood flow rate in the region of interest is less than the second contrast injection flow rate and greater than the first contrast injection flow rate, for instance that it is an average or other combination of the first and second contrast injection flow rates.

In the case where the predetermined condition is the onset of a steady state pixel density, the second contrast injection flow rate can also be used is a variety of ways to determine the blood flow rate in the region of interest. As one example, the second contrast injection flow rate can be used to determine the blood flow rate in the region of interest by determining that the blood flow rate in the vessel approximates the second contrast injection flow rate. As another example, the second contrast injection flow rate can be used to determine the blood flow rate in the region of interest by determining that the blood flow rate in the vessel is greater than the second contrast injection flow rate but less than a third contrast injection flow rate that is greater than the second contrast injection flow rate.

Non-transitory computer-readable storage article embodiments can also be used for determining a blood flow rate in a region of interest using one or more contrast injection flow rates. In various embodiments of such a non-transitory computer-readable storage article, one or more of the details provided above in reference to FIGS. 5A-7 can be implemented in computer-executable instructions stored on the non-transitory computer-readable storage article.

For example, one such embodiment can include a non-transitory computer-readable storage article having computer-executable instructions stored thereon to cause at least one programmable processor to analyze first image data representing a first region of interest acquired at a first acquisition time to determine if a first contrast injection flow rate at which contrast media was injected into a vessel has caused a predetermined condition to be present in the first image data. This article embodiment also has computer-executable instructions stored thereon to cause at least the one programmable processor to analyze second image data representing the first region of interest acquired at a second acquisition time to determine if a second contrast injection flow rate at which contrast media was injected into the vessel and which is greater than the first contrast injection flow rate has caused the predetermined condition to be present in the second image data. And, this article embodiment also has computer-executable instructions stored thereon to cause at least the one programmable processor to, upon determining that the predetermined condition is present in the second image data, use the second contrast injection flow rate to determine a blood flow rate in the vessel. One or more other features disclosed above in reference to FIGS. 5A-7 can also be incorporated into this particular non-transitory computer-readable storage article embodiment or other non-transitory computer-readable storage article embodiments. For example, the features disclosed with respect to the predetermined condition being the presence of contrast media flowing out of the coronary artery back into the aorta or the onset of a steady state pixel density can be included.

Figure 8:
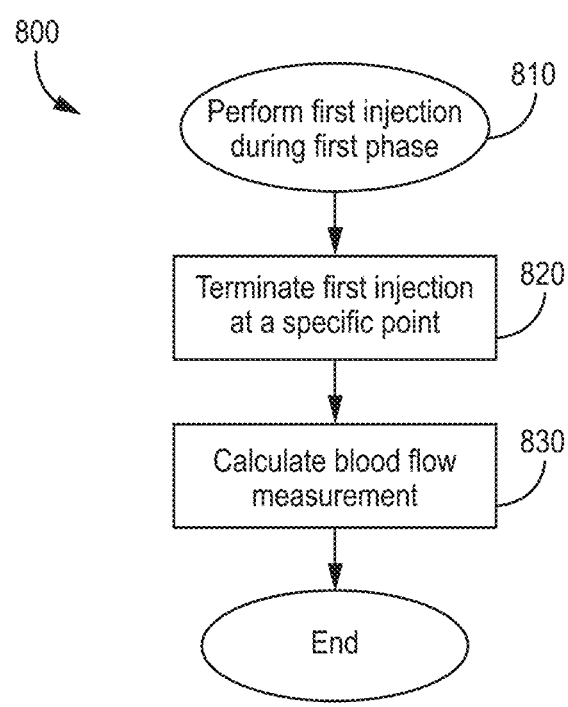
FIG. 8 is a flow diagram of an embodiment of a method for determining a blood flow measurement in a region of interest using a contrast injection performed during a particular phase of a cardiac cycle.

FIG. 8 shows a flow diagram of an embodiment of a method 800 for determining a blood flow measurement in a region of interest by analyzing image data associated with one or more contrast injections that are synchronized to the cardiac cycle. For example, the method 800 can determine a blood flow measurement in a region of interest by analyzing image data associated with one or more contrast injections that are performed during a particular phase of a cardiac cycle.

At step 810, a first injection of contrast media into a vessel is performed during one of a systolic phase and a diastolic phase of a cardiac cycle. As one example, the first injection of contrast media into the vessel can be performed during the systolic phase of the cardiac cycle. In another example, the first injection of contrast media into the vessel can be performed during the diastolic phase of the cardiac cycle.

Figure 9A:
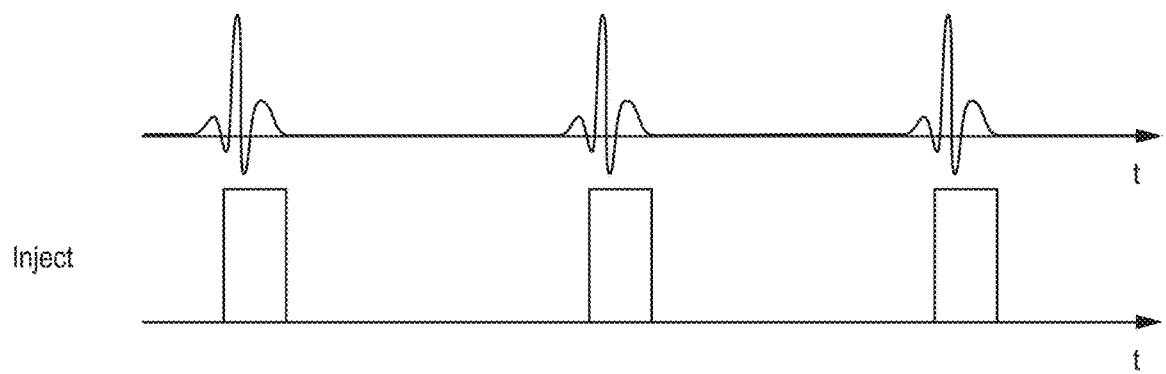
FIGS. 9A-9B are schematic timing diagrams showing an ECG and contrast media injections.
Figure 9B:
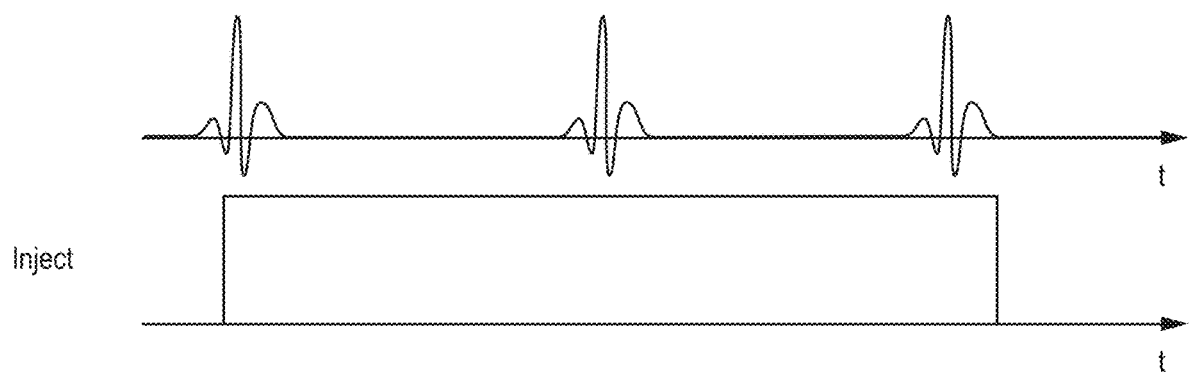

At step 820, the first injection of contrast media is terminated at a specific point (e.g., prior to the beginning of the other of the systolic and the diastolic phase of the cardiac cycle (FIG. 9A), after one or more subsequent phases of the cardiac cycle (FIG. 9B), etc.). In the example where the first injection of contrast media into the vessel is performed during the systolic phase of the cardiac cycle at step 810, step 820 can include terminating the first injection of contrast media prior to the beginning of the diastolic phase of the cardiac cycle. In this example, it can be the case that no contrast media is injected during an entirety of the diastolic phase of the cardiac cycle and even that no fluid is injected during the entirety of the diastolic phase of the cardiac cycle. Though it can instead be the case that, when the first injection of contrast media into the vessel is performed during the systolic phase and terminated prior to the beginning of the diastolic phase, the method 800 can include another step of performing a second injection of the contrast media into the vessel after terminating the first injection and during the diastolic phase of the cardiac cycle.

At step 830, after terminating the first injection at step 820, a blood flow measurement for a first region of a vessel is calculated based on image data representing the contrast media at the first region. For example, calculating the blood flow measurement for the region of the vessel, after terminating the first injection, can include calculating the blood flow measurement for the vessel at a native blood flow for the region of the vessel. The native blood flow, in some cases, can be considered to be a blood flow that is present in the vessel at a time when no fluid injection is being performed at the vessel. Thus, a native blood flow calculated at step 830 can be a blood flow measurement calculated without any forced flow bias caused by a fluid injection at the vessel acting to artificially increase the flow at the vessel. As detailed further below, examples provided herein can act to provide a native blood flow calculation.

In one example, at step 830, when the first injection is performed during the systolic phase and terminated prior to the beginning of the diastolic phase, the image data used to calculate the blood flow measurement can be image data acquired after terminating the first injection and during the diastolic phase. In such an example, the method 800 can use a systolic phase synchronized contrast injection to calculate a blood flow measurement for a region of a vessel corresponding to the diastolic phase. In this example, the image data may include a plurality of image frames acquired during the diastolic phase. Then, to calculate the blood flow measurement for the region of the vessel based on this image data, a frame counting process can be implemented which counts the number of image frames it takes for the contrast media injected during the systolic phase to travel a known length within the vessel during the diastolic phase. For instance, a number of image frames, within the plurality of image frames, over which the contrast media travels a distance from a first predetermined location in the region of the vessel to a second predetermined location in the region of the vessel can be measured (e.g., counted). A time corresponding to the measured number of image frames can be determined and a blood flow velocity for the region of the vessel can be calculated by dividing the distance by the determined time. Depending on the application, a time corresponding to the measured number of image frames can be determined by multiplying a known interval of time corresponding to each image frame over which the contrast media travels the distance by the measured number of image frames. The known interval of time corresponding to each image frame can vary depending on the imaging device used to acquire the image data.

Thus, in this example, contrast media can be injected during the systolic phase of the cardiac cycle such that one or more contrast boluses are pre-loaded into a proximal area of the vessel during the systolic, relatively low flow, phase of the cardiac cycle. This can be done, for instance, using a contrast injection synchronized so as to begin and end within the systolic phase such that no contrast media injection is made during the diastolic phase. Once the contrast is pre-loaded and the systolic phase comes to an end, the injection can be stopped and then at this point, the increased flow of blood during diastolic phase can carry the contrast bolus through the vessel (e.g., coronary artery) at the native blood flow. The contrast bolus flow during the diastolic phase can be used in a frame count analysis of angiographic image data to measure the blood flow velocity for the vessel, as noted above. Notably, contrast media injection synchronized with the systolic phase may allow for a more accurate frame count analysis to occur when measuring blood flow velocity since it can avoid imparting a forced flow bias on the native blood flow as may otherwise occur with unsynchronized contrast media injections at a high pressure.

The calculated blood flow measurement corresponding to the diastolic phase can be used to determine a number of various diagnostic metrics. For instance, the calculated blood flow measurement corresponding to the diastolic phase can be used to model pressure ratios useful for diagnostic purposes relating to vessel flow, including the severity of a constriction in a vessel. In one such application, the calculated blood flow measurement corresponding to the diastolic phase can be used to determine an instantaneous wave-free ratio ("iFR"). In another such application, the calculated blood flow measurement corresponding to the diastolic phase can be used to determine a diastolic pressure ratio ("dPR").

In another example, contrast media injections can be synchronized with both of the diastolic and systolic phases to enable discrete flow analysis during each of the diastolic and systolic phases. When the first injection of contrast media into the vessel is performed during the systolic phase and terminated prior to the beginning of the diastolic phase, the method 800 can include another step of performing a second injection of contrast media into the vessel after terminating the first injection and during the diastolic phase of the cardiac cycle. This second injection of contrast media into the vessel can be terminated prior to the beginning of the next systolic phase of the cardiac cycle. And, after terminating the second injection, the blood flow measurement for the region of the vessel can be calculated based on image data representing the contrast media at the region of the vessel.

In particular, in such an example, as noted, the blood flow measurement at the region of the vessel can be calculated for each of the diastolic and systolic phases. The image data used to calculate the flow velocity for each phase can include a plurality of image frames, and the plurality of image frames can include a first set of image frames acquired during the systolic phase and a second set of image frames acquired during the diastolic phase. A blood flow velocity for the region of the vessel can then be calculated based on this image data by calculating a first blood flow velocity for the region of the vessel based on the first set of image frames acquired during the systolic phase and calculating a second blood flow velocity for the region of the vessel based on the second set of image frames acquired during the diastolic phase.

Thus, in the examples provided in reference to the embodiment of FIG. 8, contrast media injections can be synchronized with one or each of the diastolic phase and the systolic phase of the cardiac cycle to enable discrete analysis of flow during one or each of the diastolic phase and the systolic phase. That is, in these examples, contrast media injections can be synchronized so as to begin and end within the systolic phase and/or to begin and end within the diastolic phase. Because flow characteristics may vary significantly in the diastolic and systolic phases, synchronizing one or more contrast media injections so that a contrast media injection does not span from diastole to systole, or vice versa, can allow for flow analysis using the injected contrast media confined to the conditions of one of diastole or systole. This may allow for more accurate flow estimation individualized to one or each of these two phases and thereby improve empirical flow models used to characterize stenoses in coronary arteries.

Non-transitory computer-readable storage article embodiments can also be used for determining a blood flow measurement in a region of interest by analyzing image data associated with one or more contrast injections that are synchronized with one or both of a systolic or diastolic phase of the cardiac cycle. In various embodiments of such a non-transitory computer-readable storage article, one or more of the details provided above in reference to FIG. 8 can be implemented in computer-executable instructions stored on the non-transitory computer-readable storage article.

For example, one such embodiment can include a non-transitory computer-readable storage article having computer-executable instructions stored thereon to cause at least one programmable processor to calculate a blood flow measurement for a first region of a vessel based on image data representing injected contrast media at the first region. In this article embodiment, computer-executable instructions stored thereon cause the at least one programmable processor to base the blood flow measurement calculation on image data representing contrast media injected into the vessel during one of a systolic phase and a diastolic phase of a cardiac cycle and terminated at a specific point (e.g., prior to the beginning of the other of the systolic phase and the diastolic phase of the cardiac cycle (FIG. 9A), after one or more subsequent phases of the cardiac cycle (FIG. 9B), etc.). One or more other features disclosed above in reference to FIG. 8 can also be incorporated into this particular non-transitory computer-readable storage article embodiment or other non-transitory computer-readable storage article embodiments. For example, the features disclosed with respect to image data corresponding to contrast media injections synchronized with one or each of the diastolic phase and the systolic phase of the cardiac cycle and discrete analysis of flow during one or each of the diastolic phase and the systolic phase can be included.

It is to be understood that the term "non-transitory," as used herein, is a limitation of the medium itself (e.g., tangible, not a signal) as opposed to a limitation on data storage persistency (e.g., RAM vs. ROM).

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A method for determining a blood flow velocity in a vessel, the method comprising the steps of:
   injecting pulsed contrast boluses into the vessel at a known frequency by injecting a first bolus of contrast media into the vessel over a first time, terminating injection of contrast media over a second time that is after the first time, injecting a second bolus of contrast media into the vessel over a third time that is after the second time, terminating injection of contrast media over a fourth time that is after the third time, and injecting a third bolus of contrast media into the vessel over a fifth time that is after the fourth time;
   analyzing image data representing a first region of the vessel to determine a distance between the first bolus of contrast media and the second bolus of contrast media in the vessel;
   calculating the blood flow velocity for the first region of the vessel by multiplying the determined distance between the first bolus of contrast media and the second bolus of contrast media by the known frequency;
   analyzing image data representing a second region of the vessel to determine a distance between the second bolus of contrast media and the third bolus of contrast media in the vessel;
   calculating the blood flow velocity for the second region of the vessel by multiplying the determined distance between the second bolus of contrast media and the third bolus of contrast media by the known frequency; and
   comparing the calculated blood flow velocity for the first region of the vessel to the calculated blood flow velocity for the second region of the vessel to determine whether a difference between the calculated blood flow velocity for the first region of the vessel and the calculated blood flow velocity for the second region of the vessel exceeds a predetermined flow velocity differential threshold.

2. The method of claim 1, wherein analyzing image data representing the first region of the vessel comprises analyzing peak pixel density of the image data representing the first region of the vessel to determine a position of the first bolus of contrast media in the first region of the vessel and a position of the second bolus of contrast media in the first region of the vessel.

3. The method of claim 1, wherein the image data representing the first region of the vessel is a single frame of image data of the first region of the vessel.

4. The method of claim 1,
wherein the image data representing the first region of the vessel includes a first frame of image data representing the first region of the vessel acquired at a first acquisition time and a second frame of image data representing the first region of the vessel acquired at a second acquisition time, and
wherein determining the distance between the first bolus of contrast media and the second bolus of contrast media comprises:
analyzing the first frame of image data to determine a first distance between the first bolus of contrast media and the second bolus of contrast media in the first frame of image data;
analyzing the second frame of image data to determine a second distance between the first bolus of contrast media and the second bolus of contrast media in the second frame of image data; and
averaging the first distance and the second distance to determine the distance between the first bolus of contrast media and the second bolus of contrast media.

5. The method of claim 1, further comprising injecting saline fluid into the vessel over the second time such that saline fluid is present in the vessel between the first bolus of contrast media and the second bolus of contrast media.

6. The method of claim 1, wherein the known frequency is between 5 Hz and 20 Hz, and wherein the first time comprises between 10% and 50% of a total of the first time and the second time.

7. A method for determining a blood flow rate in a vessel, the method comprising the steps of:
injecting contrast media into the vessel at a first contrast injection flow rate;
analyzing first image data representing a first region of interest acquired at a first acquisition time, wherein analyzing the first image data comprises determining a first pixel density value associated with the first image data, to determine if the first contrast injection flow rate has caused a predetermined condition to be present in the first image data;
injecting contrast media into the vessel at a second contrast injection flow rate that is greater than the first contrast injection flow rate;
analyzing second image data representing the first region of interest acquired at a second acquisition time, wherein analyzing the second image data comprises determining a second pixel density value associated with the second image data, to determine if the second contrast injection flow rate has caused the predetermined condition to be present in the second image data;
injecting contrast media into the vessel at a third contrast injection flow rate that is greater than the second contrast injection flow rate;
analyzing third image data representing the first region of interest acquired at a third acquisition time, wherein analyzing the third image data comprises determining a third pixel density value associated with the third image data, to determine if the third contrast injection flow rate has caused the predetermined condition to be present in the third image data; and
upon determining that the predetermined condition is present in the third image data, determining that the blood flow rate in the vessel approximates the second contrast injection flow rate,
wherein the predetermined condition is an onset of a steady state pixel density, and wherein determining that the predetermined condition is present in the third image data comprises determining that the second pixel density value differs from the first pixel density value by more than a predetermined threshold while the third pixel density value differs from the second pixel density value by less than the predetermined threshold.

8. The method of claim 7, wherein using the second contrast injection flow rate to determine the blood flow rate in the vessel comprises determining that the blood flow rate in the vessel approximates the second contrast injection flow rate.

9. The method of claim 7, wherein the first region of interest is an area of myocardium fed by a coronary artery.

10. A method for determining a blood flow measurement in a vessel, the method comprising the steps of:
performing a first injection of a contrast media into the vessel during one of a systolic phase and a diastolic phase of a cardiac cycle;
terminating the first injection of the contrast media prior to the beginning of the other of the systolic phase and the diastolic phase of the cardiac cycle;
after terminating the first injection, calculating the blood flow measurement for a region of the vessel based on image data representing the contrast media at the region;
performing a second injection of the contrast media into the vessel during the other of the systolic phase and the diastolic phase of the cardiac cycle;
terminating the second injection of the contrast media prior to the beginning of the one of the systolic phase and the diastolic phase of the cardiac cycle; and
after terminating the second injection, calculating the blood flow measurement for the region of the vessel based on image data representing the contrast media at the region;
wherein the image data comprises a plurality of image frames that includes a first set of image frames acquired during the one of the systolic phase and the diastolic phase of the cardiac cycle, and a second set of image frames acquired during the other of the systolic phase and the diastolic phase of the cardiac cycle, and
wherein calculating the blood flow measurement for the region of the vessel based on the image data comprises:
calculating a first blood flow velocity for the region of the vessel based on the first set of image frames acquired during the one of the systolic phase and the diastolic phase of the cardiac cycle; and
calculating a second blood flow velocity for the region of the vessel based on the second set of image frames acquired during the other of the systolic phase and the diastolic phase of the cardiac cycle.

11. The method of claim 10, wherein the first injection of the contrast media is performed during the systolic phase, and wherein the first injection of the contrast media is terminated prior to the beginning of the diastolic phase.

12. The method of claim 11, wherein the image data is acquired after terminating the first injection and during the diastolic phase.

13. The method of claim 12,
wherein the image data comprises a plurality of image frames, and
wherein calculating the blood flow measurement for the region of the vessel based on the image data comprises:
   measuring a number of image frames, within the plurality of image frames, over which the contrast media travels a distance from a first predetermined location in the region of the vessel to a second predetermined location in the region of the vessel;
   determining a time corresponding to the measured number of image frames; and
   calculating a blood flow velocity for the region of the vessel by dividing the distance by the determined time.

14. The method of claim 13, wherein the calculated blood flow velocity corresponds to the diastolic phase, and the method further comprises using the calculated blood flow velocity to determine an instantaneous wave-free ratio.

15. The method of claim 13, wherein the calculated blood flow velocity corresponds to the diastolic phase, and the method further comprises using the calculated blood flow velocity to determine a diastolic pressure ratio.

16. The method of claim 10, wherein calculating the blood flow measurement for the region of the vessel after terminating the first injection comprises calculating the blood flow measurement for the region of the vessel at a native blood flow for the region of the vessel, and wherein the native blood flow is present at a time when no injection is being performed at the vessel.

17. The method of claim 10, wherein terminating the first injection of the contrast media occurs after the beginning of the other of the systolic phase and the diastolic phase of the cardiac cycle.

* * * * *